(12) United States Patent
Popp et al.

(10) Patent No.: US 9,980,859 B2
(45) Date of Patent: May 29, 2018

(54) ABSORBENT ARTICLE HAVING A FASTENING SYSTEM WITH IMPROVED FLEXIBILITY

(71) Applicant: Kimberly-Clark Worldwide, Inc., Neenah, WI (US)

(72) Inventors: Robert Lee Popp, Greenville, WI (US); David Fleger Bishop, Appleton, WI (US); David John Enz, Neenah, WI (US); Catherine Marguerite Hancock-Cooke, Neenah, WI (US); Wendy Lynn VanDyke, Appleton, WI (US); Alanna Nicole Haessler, Appleton, WI (US); Jeffrey Alan DeBroux, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 587 days.

(21) Appl. No.: 14/169,331

(22) Filed: Jan. 31, 2014

(65) Prior Publication Data

US 2015/0216743 A1 Aug. 6, 2015

(51) Int. Cl.
*A61F 13/15* (2006.01)
*A61F 13/56* (2006.01)

(52) U.S. Cl.
CPC ...... *A61F 13/5644* (2013.01); *A61F 13/5638* (2013.01)

(58) Field of Classification Search
CPC .................... A61F 13/5644; A61F 13/5368
USPC .................... 604/391, 387, 386, 394, 396
See application file for complete search history.

(56) References Cited

U.S. PATENT DOCUMENTS

| 3,848,594 | A | 11/1974 | Buell |
| 4,010,754 | A | 3/1977 | Pieniak |
| 4,041,203 | A | 8/1977 | Brock et al. |
| 4,050,462 | A | 9/1977 | Woon et al. |

(Continued)

FOREIGN PATENT DOCUMENTS

| EP | 0 217 032 A2 | 4/1987 |
| EP | 0 233 704 B1 | 7/1992 |

(Continued)

OTHER PUBLICATIONS

Co-pending U.S. Appl. No. 13/953,364, filed Jul. 29, 2013, by Popp et al. for "Tailored Peel for Secondary Fastener to Optimize Ease of Opening Product."

(Continued)

*Primary Examiner* — Jacqueline Stephens
(74) *Attorney, Agent, or Firm* — Kimberly-Clark Worldwide, Inc.

(57) ABSTRACT

An absorbent article is provided that can include a fastening system configured to attach the rear waist region to the front waist region to define a wear configuration of the absorbent article. The fastening system can comprise a primary fastening system and a secondary fastening system, the secondary fastening system including at least one secondary first fastening component and at least one secondary second fastening component. A region of flexibility can be provided between adjacent components of the absorbent article between the at least one secondary first fastening component and the bodyside liner in an area under the at least one secondary first fastening component.

28 Claims, 10 Drawing Sheets

(56) References Cited

U.S. PATENT DOCUMENTS

| | | | |
|---|---|---|---|
| 4,253,461 A | 3/1981 | Strickland et al. | |
| 4,374,888 A | 2/1983 | Bornslaeger | |
| 4,402,690 A | 9/1983 | Redfern | |
| 4,500,316 A | 2/1985 | Damico | |
| 4,581,772 A | 4/1986 | Smith | |
| 4,585,448 A | 4/1986 | Enloe | |
| 4,662,875 A | 5/1987 | Hirotsu et al. | |
| 4,663,220 A | 5/1987 | Wisneski et al. | |
| 4,699,622 A | 10/1987 | Toussant et al. | |
| 4,701,179 A | 10/1987 | Kellenberger et al. | |
| 4,704,116 A * | 11/1987 | Enloe ............... A61F 13/49009 604/358 | |
| 4,753,650 A | 6/1988 | Williams | |
| 4,766,029 A | 8/1988 | Brock et al. | |
| 4,770,656 A | 9/1988 | Proxmire et al. | |
| 4,773,906 A | 9/1988 | Krushel | |
| 4,801,298 A | 1/1989 | Sorenson et al. | |
| 4,846,815 A | 7/1989 | Scripps | |
| 4,850,988 A | 7/1989 | Aledo et al. | |
| 4,850,992 A | 7/1989 | Amaral et al. | |
| 4,869,724 A | 9/1989 | Scripps | |
| 4,894,060 A | 1/1990 | Nestegard | |
| 4,923,456 A | 5/1990 | Proxmire | |
| 4,936,840 A | 6/1990 | Proxmire | |
| 4,938,753 A | 7/1990 | Van Gompel et al. | |
| 4,940,464 A | 7/1990 | Van Gompel et al. | |
| 4,946,527 A | 8/1990 | Battrell | |
| 4,988,346 A | 1/1991 | Pfefferkorn | |
| 5,019,072 A | 5/1991 | Polski | |
| 5,019,073 A | 5/1991 | Roessler et al. | |
| 5,046,272 A | 9/1991 | Vogt et al. | |
| 5,069,678 A | 12/1991 | Yamamoto et al. | |
| 5,104,116 A | 4/1992 | Pohjola | |
| 5,108,384 A | 4/1992 | Goulait | |
| 5,151,092 A | 9/1992 | Buell et al. | |
| 5,169,706 A | 12/1992 | Collier, IV et al. | |
| 5,176,670 A | 1/1993 | Roessler et al. | |
| 5,176,671 A | 1/1993 | Roessler et al. | |
| 5,213,881 A | 5/1993 | Timmons et al. | |
| 5,224,405 A | 7/1993 | Pohjola | |
| 5,226,992 A | 7/1993 | Morman | |
| 5,231,738 A | 8/1993 | Higashinaka | |
| 5,234,423 A | 8/1993 | Alemany et al. | |
| 5,242,436 A | 9/1993 | Weil et al. | |
| 5,260,015 A | 11/1993 | Kennedy et al. | |
| 5,279,604 A | 1/1994 | Robertson et al. | |
| 5,325,569 A | 7/1994 | Goulait et al. | |
| 5,358,500 A | 10/1994 | Lavon et al. | |
| 5,368,585 A | 11/1994 | Dokken | |
| 5,370,634 A | 12/1994 | Ando et al. | |
| 5,383,871 A | 1/1995 | Carlin et al. | |
| 5,392,498 A | 2/1995 | Gouliait et al. | |
| 5,399,219 A | 3/1995 | Roessler et al. | |
| 5,403,302 A | 4/1995 | Roessler et al. | |
| 5,409,476 A | 4/1995 | Coates | |
| 5,423,789 A | 6/1995 | Kuen | |
| 5,464,688 A | 11/1995 | Timmons et al. | |
| 5,518,795 A | 5/1996 | Kennedy et al. | |
| 5,531,732 A | 7/1996 | Wood | |
| 5,554,143 A | 9/1996 | Roe et al. | |
| 5,593,401 A | 1/1997 | Sosalla et al. | |
| 5,599,338 A | 2/1997 | Enloe | |
| 5,603,794 A | 2/1997 | Thomas et al. | |
| 5,605,735 A | 2/1997 | Zehner et al. | |
| 5,611,789 A | 3/1997 | Seth | |
| 5,624,428 A | 4/1997 | Sauer | |
| 5,624,429 A | 4/1997 | Long et al. | |
| 5,643,651 A | 7/1997 | Murasaki | |
| H1674 H | 8/1997 | Ames et al. | |
| 5,669,120 A | 9/1997 | Wessels et al. | |
| 5,674,215 A | 10/1997 | Roennberg | |
| 5,685,873 A | 11/1997 | Bruemmer | |
| 5,744,080 A | 4/1998 | Kennedy et al. | |
| 5,759,317 A | 6/1998 | Justmann | |
| 5,766,389 A | 6/1998 | Brandon et al. | |
| 5,766,723 A | 6/1998 | Oborny et al. | |
| 5,782,819 A | 7/1998 | Tanzer et al. | |
| 5,797,896 A | 8/1998 | Schmitz | |
| 5,830,206 A | 11/1998 | Larsson | |
| 5,846,262 A | 12/1998 | Sayama et al. | |
| 5,851,467 A | 12/1998 | Murasaki | |
| 5,858,515 A | 1/1999 | Stokes et al. | |
| 5,984,911 A | 11/1999 | Siebers et al. | |
| 5,997,522 A | 12/1999 | Provost et al. | |
| 6,030,373 A | 2/2000 | VanGompel et al. | |
| 6,045,543 A | 4/2000 | Pozniak et al. | |
| 6,056,732 A | 5/2000 | Fujioka et al. | |
| 6,063,066 A | 5/2000 | Inoue et al. | |
| 6,099,516 A | 8/2000 | Pozniak et al. | |
| 6,102,901 A | 8/2000 | Lord et al. | |
| 6,142,983 A | 11/2000 | Surprise et al. | |
| 6,142,986 A | 11/2000 | Lord et al. | |
| 6,174,303 B1 | 1/2001 | Surprise et al. | |
| 6,174,476 B1 | 1/2001 | Kennedy et al. | |
| 6,248,419 B1 | 6/2001 | Kennedy et al. | |
| 6,264,644 B1 | 7/2001 | Igaue et al. | |
| 6,287,287 B1 | 9/2001 | Elsberg | |
| 6,302,871 B1 | 10/2001 | Nakao et al. | |
| 6,322,552 B1 | 11/2001 | Blenke et al. | |
| 6,371,949 B1 | 4/2002 | Soga et al. | |
| 6,371,951 B1 | 4/2002 | Koczab et al. | |
| 6,387,085 B1 | 5/2002 | Van Gompel et al. | |
| 6,402,731 B1 | 6/2002 | Surprise et al. | |
| 6,406,466 B1 | 6/2002 | Pozniak et al. | |
| 6,454,752 B1 | 9/2002 | Huang et al. | |
| 6,491,675 B1 | 12/2002 | Shimada et al. | |
| 6,508,797 B1 | 1/2003 | Pozniak et al. | |
| 6,524,293 B1 | 2/2003 | Elsberg et al. | |
| 6,544,242 B1 | 4/2003 | Kido et al. | |
| 6,551,294 B1 | 4/2003 | Elsberg et al. | |
| 6,554,816 B1 | 4/2003 | Olson | |
| 6,572,601 B2 | 6/2003 | Suprise et al. | |
| 6,595,977 B1 | 7/2003 | Luizzi, Jr. et al. | |
| 6,613,032 B2 | 9/2003 | Ronnberg et al. | |
| 6,648,866 B2 | 11/2003 | Magee et al. | |
| 6,682,512 B2 | 1/2004 | Uitenbroek et al. | |
| 6,730,069 B2 | 5/2004 | Tanzer et al. | |
| 6,733,483 B2 | 5/2004 | Raufman et al. | |
| 6,736,804 B1 | 5/2004 | Robertson et al. | |
| 6,737,147 B2 | 5/2004 | Kennedy et al. | |
| 6,849,067 B2 | 2/2005 | Fletcher et al. | |
| 6,890,630 B2 | 5/2005 | Franklin et al. | |
| 6,893,426 B1 | 5/2005 | Popp et al. | |
| 6,916,750 B2 | 7/2005 | Thomas et al. | |
| 6,932,802 B2 | 8/2005 | Luizzi, Jr. et al. | |
| 6,945,968 B2 | 9/2005 | Svensson et al. | |
| 6,972,012 B1 | 12/2005 | Pozniak et al. | |
| 6,976,978 B2 | 12/2005 | Ruman et al. | |
| 6,994,697 B2 | 2/2006 | Shimada et al. | |
| 6,994,698 B2 | 2/2006 | Leak et al. | |
| 7,014,906 B2 | 3/2006 | Tuman et al. | |
| 7,018,368 B2 | 3/2006 | Van Gompel et al. | |
| 7,032,278 B2 | 4/2006 | Kurtz, Jr. | |
| 7,122,024 B2 | 10/2006 | Nakajima et al. | |
| 7,150,730 B2 | 12/2006 | Hasler et al. | |
| 7,150,732 B2 | 12/2006 | Yoshida et al. | |
| 7,150,733 B2 | 12/2006 | Yamakawa et al. | |
| 7,156,833 B2 | 1/2007 | Couture-Dorscher et al. | |
| 7,162,780 B2 | 1/2007 | Martin et al. | |
| 7,175,584 B2 | 2/2007 | Maxton et al. | |
| 7,189,220 B2 | 3/2007 | Miyoshi et al. | |
| 7,198,621 B2 | 4/2007 | Moser et al. | |
| 7,201,744 B2 | 4/2007 | Van Gompel et al. | |
| 7,207,979 B2 | 4/2007 | Price et al. | |
| 7,211,072 B2 | 5/2007 | Nawata et al. | |
| 7,244,382 B2 | 7/2007 | Tachauer et al. | |
| 7,252,658 B2 | 8/2007 | Sayama | |
| 7,275,290 B2 | 10/2007 | Clarner et al. | |
| 7,344,525 B2 | 3/2008 | Linker, III et al. | |
| 7,422,783 B2 | 9/2008 | Tremblay et al. | |
| 7,449,017 B2 | 11/2008 | Yoshida | |
| 7,451,532 B2 | 11/2008 | Provost et al. | |
| 7,455,665 B2 | 11/2008 | Wendelstorf et al. | |
| 7,473,818 B2 | 1/2009 | Datta et al. | |

(56) References Cited

U.S. PATENT DOCUMENTS

| | | |
|---|---|---|
| 7,534,481 B2 | 5/2009 | Seth et al. |
| 7,568,264 B2 | 8/2009 | Miyamoto et al. |
| 7,569,042 B2 | 8/2009 | Van Gompel et al. |
| 7,662,137 B2 | 2/2010 | Sayama et al. |
| 7,736,351 B2 | 6/2010 | Nigam et al. |
| 7,811,273 B2 | 10/2010 | Kline et al. |
| 7,828,784 B2 | 11/2010 | Popp et al. |
| 7,855,314 B2 | 12/2010 | Hanao et al. |
| 8,118,801 B2 | 2/2012 | Macura et al. |
| 8,211,077 B2 | 7/2012 | Sugiyama et al. |
| 8,353,891 B2 | 1/2013 | Hornung et al. |
| 8,395,017 B2 | 3/2013 | Nakahata et al. |
| 8,496,640 B2 | 7/2013 | Molander |
| 8,636,710 B2 | 1/2014 | Ellingson et al. |
| 2002/0016581 A1 | 2/2002 | Kline et al. |
| 2002/0032427 A1 | 3/2002 | Schmitz et al. |
| 2002/0095130 A1 | 7/2002 | Seitter et al. |
| 2002/0095132 A1 | 7/2002 | Ashton et al. |
| 2002/0107498 A1 | 8/2002 | Kling et al. |
| 2002/0123734 A1 | 9/2002 | Carlbark et al. |
| 2002/0138064 A1 | 9/2002 | Datta et al. |
| 2002/0165518 A1 | 11/2002 | Datta et al. |
| 2002/0169431 A1 | 11/2002 | Kline et al. |
| 2002/0173768 A1 | 11/2002 | Elsberg et al. |
| 2002/0174934 A1 | 11/2002 | Johnson et al. |
| 2003/0044578 A1 | 3/2003 | Nissing |
| 2003/0124303 A1 | 7/2003 | Price et al. |
| 2003/0153891 A1 | 8/2003 | Molee |
| 2003/0233080 A1 | 12/2003 | Backman et al. |
| 2004/0102745 A1* | 5/2004 | Linker, III ............ A61F 13/622 604/356 |
| 2004/0122400 A1 | 6/2004 | Hancock et al. |
| 2004/0122413 A1 | 6/2004 | Roessler et al. |
| 2004/0129592 A1 | 7/2004 | Otsubo |
| 2004/0153046 A1 | 8/2004 | Ito et al. |
| 2004/0158224 A1 | 8/2004 | Kline et al. |
| 2004/0187275 A1 | 9/2004 | Kennedy et al. |
| 2004/0243091 A1 | 12/2004 | Mitsui et al. |
| 2004/0261233 A1 | 12/2004 | Kingsford et al. |
| 2005/0015069 A1 | 1/2005 | Hamilton et al. |
| 2005/0027271 A1 | 2/2005 | Popp et al. |
| 2005/0043700 A1 | 2/2005 | Otsubo et al. |
| 2005/0090793 A1 | 4/2005 | Winqvist |
| 2005/0143710 A1 | 6/2005 | Van Gompel et al. |
| 2005/0148976 A1 | 7/2005 | Van Gompel et al. |
| 2005/0148977 A1 | 7/2005 | Van Gompel et al. |
| 2005/0148982 A1 | 7/2005 | VanGompel et al. |
| 2005/0148985 A1 | 7/2005 | Bronk et al. |
| 2005/0148986 A1 | 7/2005 | Collins et al. |
| 2005/0217791 A1 | 10/2005 | Costello et al. |
| 2005/0222551 A1 | 10/2005 | Otsubo |
| 2006/0004337 A1 | 1/2006 | Datta |
| 2006/0069376 A1 | 3/2006 | Miller |
| 2006/0069378 A1 | 3/2006 | Winkel et al. |
| 2006/0241561 A1 | 10/2006 | De Angelis |
| 2006/0247594 A1 | 11/2006 | Nickel et al. |
| 2006/0247597 A1 | 11/2006 | Hogan et al. |
| 2006/0264861 A1 | 11/2006 | Lavon et al. |
| 2006/0266465 A1 | 11/2006 | Meyer |
| 2006/0293639 A1 | 12/2006 | Van Gompel et al. |
| 2007/0032773 A1 | 2/2007 | Magee et al. |
| 2007/0083177 A1 | 4/2007 | Takino et al. |
| 2007/0093769 A1 | 4/2007 | Kline et al. |
| 2007/0112321 A1 | 5/2007 | Goates et al. |
| 2007/0157441 A1 | 7/2007 | Kline et al. |
| 2007/0250026 A1 | 10/2007 | Venturino et al. |
| 2008/0058753 A1 | 3/2008 | Dalal |
| 2008/0086104 A1 | 4/2008 | Karlsson |
| 2008/0091163 A1 | 4/2008 | Fujioka |
| 2008/0097363 A1 | 4/2008 | Fernfors et al. |
| 2008/0114323 A1 | 5/2008 | Kline et al. |
| 2008/0132863 A1 | 6/2008 | Waksmundzki et al. |
| 2008/0154227 A1 | 6/2008 | Andersson et al. |
| 2008/0172840 A1 | 7/2008 | Kacker et al. |
| 2008/0312624 A1 | 12/2008 | Hundorf et al. |
| 2009/0076783 A1 | 3/2009 | Babusik et al. |
| 2009/0198207 A1 | 8/2009 | Torigoshi et al. |
| 2009/0299317 A1 | 12/2009 | Flannery |
| 2009/0299318 A1 | 12/2009 | Faulks et al. |
| 2009/0299322 A1 | 12/2009 | Faulks et al. |
| 2009/0299323 A1 | 12/2009 | Schlinz et al. |
| 2010/0234822 A1 | 9/2010 | Baeck |
| 2010/0241096 A1 | 9/2010 | Lavon et al. |
| 2010/0324517 A1 | 12/2010 | Lenhult et al. |
| 2011/0100526 A1 | 5/2011 | Umebayashi |
| 2011/0168318 A1 | 7/2011 | Nilsson et al. |
| 2012/0157958 A1 | 6/2012 | Tenorio et al. |
| 2012/0245548 A1 | 9/2012 | Matsushima et al. |
| 2013/0067701 A1 | 3/2013 | Grady et al. |
| 2013/0211361 A1 | 8/2013 | Anderson et al. |
| 2013/0310794 A1 | 11/2013 | Faulks et al. |
| 2014/0046284 A1 | 2/2014 | Dougherty, Jr. et al. |
| 2014/0046287 A1 | 2/2014 | Martin et al. |
| 2014/0350507 A1 | 11/2014 | Pariseau et al. |
| 2015/0025491 A1 | 1/2015 | Sakaguchi et al. |

FOREIGN PATENT DOCUMENTS

| | | |
|---|---|---|
| EP | 0 476 992 B1 | 7/1995 |
| EP | 0 756 855 A1 | 2/1997 |
| EP | 1 600 132 A1 | 11/2005 |
| EP | 1 299 063 B1 | 3/2006 |
| EP | 1 688 117 A1 | 8/2006 |
| EP | 2 335 504 B1 | 4/2013 |
| GB | 2 033 210 A | 5/1980 |
| JP | 01-062303 U1 | 4/1989 |
| JP | 01-092403 A | 4/1989 |
| JP | 02-088626 U1 | 7/1990 |
| JP | 07-227403 A | 8/1995 |
| JP | 08-005691 Y2 | 2/1996 |
| JP | 08-252281 A | 10/1996 |
| JP | 2003-079666 A | 3/2003 |
| JP | 2006-280664 A | 10/2006 |
| JP | 2007-209457 A | 8/2007 |
| JP | 2008-079867 A | 4/2008 |
| WO | WO 97/46197 A1 | 12/1997 |
| WO | WO 98/35642 A1 | 8/1998 |
| WO | WO 00/27328 A1 | 5/2000 |
| WO | WO 00/35397 A1 | 6/2000 |
| WO | WO 01/88245 A2 | 11/2001 |
| WO | WO 2010/135515 A1 | 11/2010 |
| WO | WO 2013/097878 A1 | 7/2013 |
| WO | WO 2013/115347 A1 | 8/2013 |

OTHER PUBLICATIONS

Co-pending U.S. Appl. No. 13/953,396, filed Jul. 29, 2013, by Hancock-Cooke et al. for "Lower Bending Stiffness of Secondary Fastener to Enhance Skin Comfort."

Co-pending U.S. Appl. No. 13/953,380, filed Jul. 29, 2013, by Stabelfeldt et al. for "Absorbent Article Having a Fastening System."

Co-pending U.S. Appl. No. 14/070,996, filed Nov. 4, 2013, by Hancock-Cooke et al. for "Improved Leg Fit Through Addition of Anchor Points to the Stretch Ear."

Co-pending U.S. Appl. No. 14/071,262, filed Nov. 4, 2013, by Stabelfeldt et al. for "Absorbent Article Having a Fastening System Adapted to Enhance Gasketing."

Co-pending U.S. Appl. No. 14/091,838, filed Nov. 27, 2013, by Collins et al. for "A Secondary Hook Feature With a Contrasting Color Appearance From the Surrounding Graphic Print."

Co-pending U.S. Appl. No. 14/144,833, filed Dec. 31, 2013, by Enz et al. for "Absorbent Article Having a Fastening System."

* cited by examiner

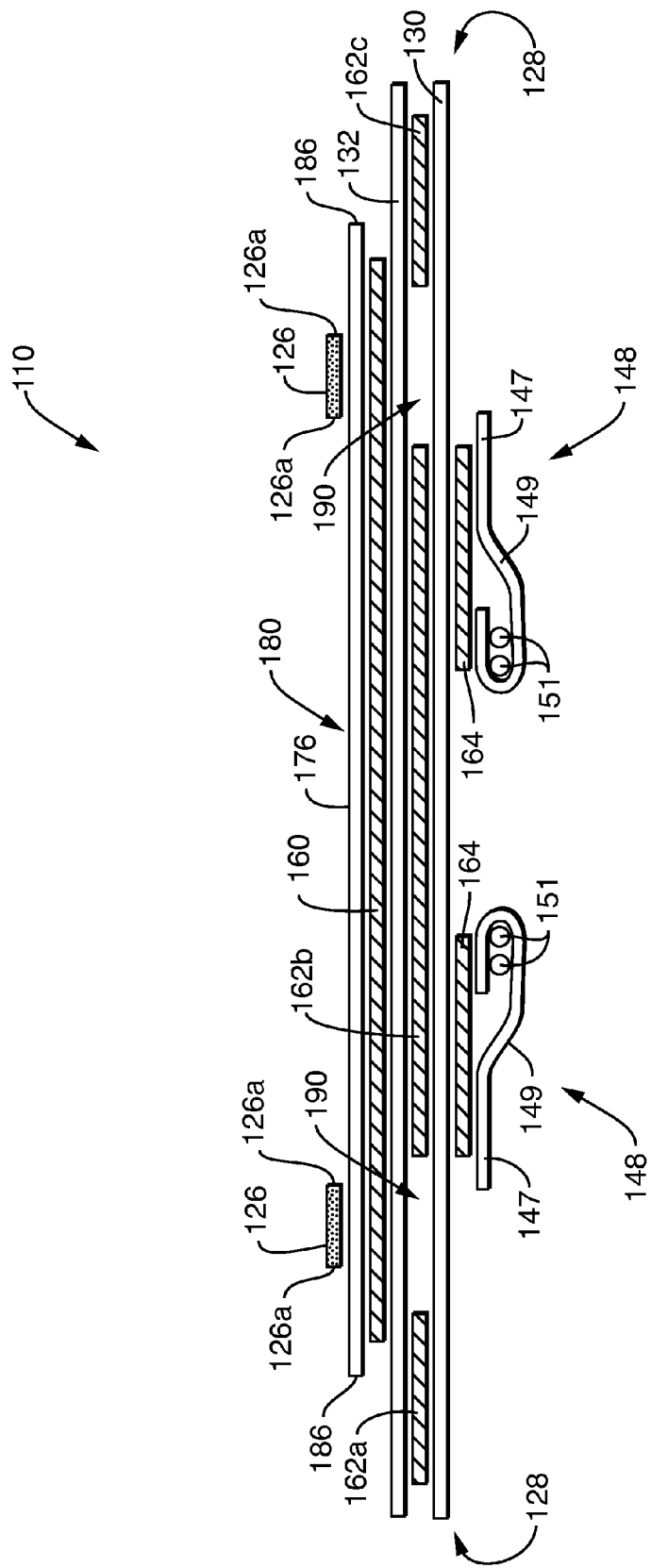

ABSORBENT ARTICLE HAVING A FASTENING SYSTEM WITH IMPROVED FLEXIBILITY

BACKGROUND

The present disclosure relates generally to absorbent articles intended for personal wear, and more particularly to disposable absorbent articles having a fastening system for selectively fastening and refastening the article about the wearer.

Many absorbent articles intended for personal wear, such as diapers, training pants, feminine hygiene products, adult incontinence products, bandages, medical garments and the like are designed to be sufficiently absorbent to absorb moisture from liquid body exudates including urine, menses, blood, etc., away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs, and left in place to absorb insults as well as to contain fecal waste.

For articles where the attachment is refastenable, such as diapers and some training pants, pop-opens (separation of the fasteners) can sometimes occur as a result of stresses placed on the attachment by movement of the wearer. For example, and particularly for absorbent articles employing only one fastening system, as an infant or other wearer of the absorbent article moves about (e.g., crawls, walks, runs, bends, etc.) the shear stress placed on the fastening system due to the infant's movement may cause fastening tabs or the like to loosen or even come unfastened completely, resulting in an absorbent article which tends to leak, sag, or fall off of a wearer.

Accordingly, some known absorbent articles comprise more than one fastening system and/or fasteners to reduce the likelihood of the article leaking, sagging, falling off the user, etc. For example, FIGS. 1-4 illustrate a known diaper, indicated generally at 10, comprising two fastening systems: a primary fastening system and a secondary fastening system. FIG. 1 depicts the diaper 10 in an unfolded and laid flat condition to show an outer cover 32 of the diaper 10 which faces away from a wearer when the diaper 10 is worn. The diaper 10 has a longitudinal direction 12 and a lateral direction 14.

In the longitudinal direction 12, the diaper 10 defines a front portion 16, a back portion 18, and a crotch portion 20 extending between and connecting the front portion 16 and the back portion 18. The diaper 10 also includes a bodyside liner 30 (facing away from the view depicted in FIG. 1 and shown in FIG. 4), and an absorbent core 34 located between the bodyside liner 30 and the outer cover 32. The diaper 10 has opposite longitudinal side edges 28 that extend between a back waist edge 38 and a front waist edge 40. The diaper 10 also includes a pair of longitudinally-extending leg cuffs 36. The leg cuffs 36 may be adapted to fit about the legs of a wearer in use and serve as a mechanical barrier to the lateral flow of body exudates.

The back portion 18 of the diaper 10 includes a pair of back ears, indicated generally at 22. Each ear 22 includes a primary first fastening component 24 as part of the primary fastening system used to secure the diaper 10 around the waist of a wearer. The primary fastening system also comprises a primary second fastening component 76 for selectively receiving and fastening to the primary first fastening components 24. For example, the diaper 10 can be selectively moved from an unfastened configuration (as seen in FIG. 2) to a fastened or wear configuration by attaching the back waist region 18 (and more specifically the back ears 22) to the front waist region 16 to define a three-dimensional wear configuration of the diaper having a waist opening and a pair of leg openings (as seen in FIG. 3). More particularly, the diaper 10 can be selectively moved from the unfastened configuration to the wear configuration by fastening the primary first fastening components 24 to the primary second fastening components 76 as is well known in the art.

The diaper 10 also includes a secondary fastening system comprising secondary first fastening components 26 and secondary second fastening components 78. For example, the illustrated diaper 10 comprises a pair of secondary first fastening components 26 as part of the front portion 16 of the diaper, with a secondary second fastening component 78 provided on each back ear 22. The primary second fastening component 76 can serve as a strip 80 or carrier material for the secondary first fastening components 26. In such configurations, when the diaper 10 is moved to the wear configuration, the secondary first fastening components 26 engage the back portion 18 of the diaper 10 (and more particularly, the secondary second fastening components 78 provided on the back ears 22) such that both the primary fastening system and the secondary fastening system secure the diaper 10 around the waist of a wearer, as is shown in FIG. 3.

However, providing the secondary first fastening components 26 on the diaper 10 may pose drawbacks when the diaper 10 is worn. For example, the secondary first fastening components 26 may lead to discomfort or decreased mobility for a wearer of the diaper 10 when the wearer moves in such a manner (e.g., crawls, walks, runs, bends, etc.) that the front portion 16 of the diaper 10 moves, bends, or otherwise deforms. There is a need, therefore, for a cost-effective and improved fastening system provided on an absorbent article which provides for increased protection against leakage and secure attachment of the absorbent article without the associated discomfort discussed above.

SUMMARY

In one aspect, an absorbent article is provided. The absorbent article generally comprises an absorbent assembly. The absorbent assembly can include a liquid impermeable outer cover, a liquid permeable bodyside liner, and an absorbent body disposed between the outer cover and the bodyside liner. The absorbent assembly can include a front waist region, a rear waist region, and a crotch region extending between the front waist region and the rear waist region. The absorbent article can further include a pair of ears extending transversely outward from opposite sides of the absorbent assembly and a fastening system configured to attach the rear waist region to the front waist region to define a wear configuration of the absorbent article. The fastening system can include a primary fastening system and a secondary fastening system. The secondary fastening system can include at least one secondary first fastening component and at least one secondary second fastening component. The at least one secondary first fastening component can be coupled to a first carrier material. The first carrier material can be coupled to the outer cover in the front waist region. At least a portion of an area of the first carrier material under the at least one secondary first fastening component is not coupled to the outer cover.

In another aspect, an absorbent article can include an absorbent assembly with a liquid impermeable outer cover, a liquid permeable bodyside liner, and an absorbent body disposed between the outer cover and the bodyside liner. The absorbent assembly can include a front waist region, a rear waist region, and a crotch region extending between the front waist region and the rear waist region. The absorbent article can further include a pair of ears extending transversely outward from opposite sides of the absorbent assembly and a fastening system configured to attach the rear waist region to the front waist region to define a wear configuration of the absorbent article. The fastening system can include a primary fastening system and a secondary fastening system. The secondary fastening system can include at least one secondary first fastening component and at least one secondary second fastening component. The at least one secondary first fastening component can be coupled to the outer cover. The bodyside liner can extend under the at least one secondary first fastening component. At least a portion of an area of the outer cover under the at least one secondary first fastening component is not coupled to the bodyside liner.

In yet another aspect, an absorbent article can include an absorbent assembly with a liquid impermeable outer cover, a liquid permeable bodyside liner, and an absorbent body disposed between the outer cover and the bodyside liner. The absorbent assembly can include a front waist region including a front waist edge, a rear waist region including a rear waist edge, a crotch region extending between the front waist region and the rear waist region, and two side edges extending between the front waist edge and the rear waist edge. The absorbent article can further include a pair of ears extending transversely outward from opposite sides of the absorbent assembly. The absorbent article can also include a pair of containment flaps on opposite sides of the absorbent body. The pair of containment flaps can include a first containment flap and a second containment flap. The first and the second containment flaps can include a stem and a base. The base can be coupled to the outer cover. The absorbent article can additionally include a fastening system configured to attach the rear waist region to the front waist region to define a wear configuration of the absorbent article. The fastening system can include a primary fastening system and a secondary fastening system. The secondary fastening system can include at least one secondary first fastening component and at least one secondary second fastening component. The at least one secondary first fastening component can be coupled to a first carrier material. The first carrier material can be coupled to the outer cover. The first containment flap can extend under the at least one secondary first fastening component. At least a portion of an area of the outer cover under the at least one secondary first fastening component is not coupled to the first containment flap, and at least a portion of an area of the first carrier material under the at least one secondary first fastening component is not coupled to the outer cover.

In still another aspect, an absorbent article can include an absorbent assembly having a liquid impermeable outer cover, a liquid permeable bodyside liner, and an absorbent body disposed between the outer cover and the bodyside liner. The absorbent assembly can include a front waist region, a rear waist region, and a crotch region extending between the front waist region and the rear waist region. The absorbent article can further include a pair of ears extending transversely outward from opposite sides of the absorbent assembly and a fastening system configured to attach the rear waist region to the front waist region to define a wear configuration of the absorbent article. The fastening system can include a primary fastening system and a secondary fastening system. The secondary fastening system can include at least one secondary first fastening component and at least one secondary second fastening component. The at least one secondary first fastening component can be coupled to a first carrier material. The first carrier material can be coupled to the outer cover in the front waist region. At least one region of flexibility can be provided between adjacent components of the absorbent article between the at least one secondary first fastening component and the bodyside liner in an area under the at least one secondary first fastening component.

BRIEF DESCRIPTION OF THE DRAWINGS

FIG. 6B is a cross-sectional view of the diaper of FIG. 5 taken along line 6-6 showing a second configuration of coupling components of the diaper under the secondary first fastening components.

Corresponding reference characters indicate corresponding parts throughout the several views of the drawings.

DETAILED DESCRIPTION OF THE DRAWINGS

According to some aspects of the disclosure, an absorbent article is provided which overcomes at least some of the deficiencies of the conventional diapers described above. More particularly, according to some aspects of the disclosure, the absorbent article includes a secondary fastening system in order to securely attach the absorbent article around the waist of a wearer, but which comprises improved pliability over known fastening systems such that the absorbent article remains securely fastened even as the wearer crawls, walks, runs, bends, etc. The secondary fastening system may be constructed of suitable materials and disposed in a suitable position relative to other components of the absorbent article such that the absorbent article may be readily packaged or used without the drawbacks of the known diapers discussed above.

Figure 5:
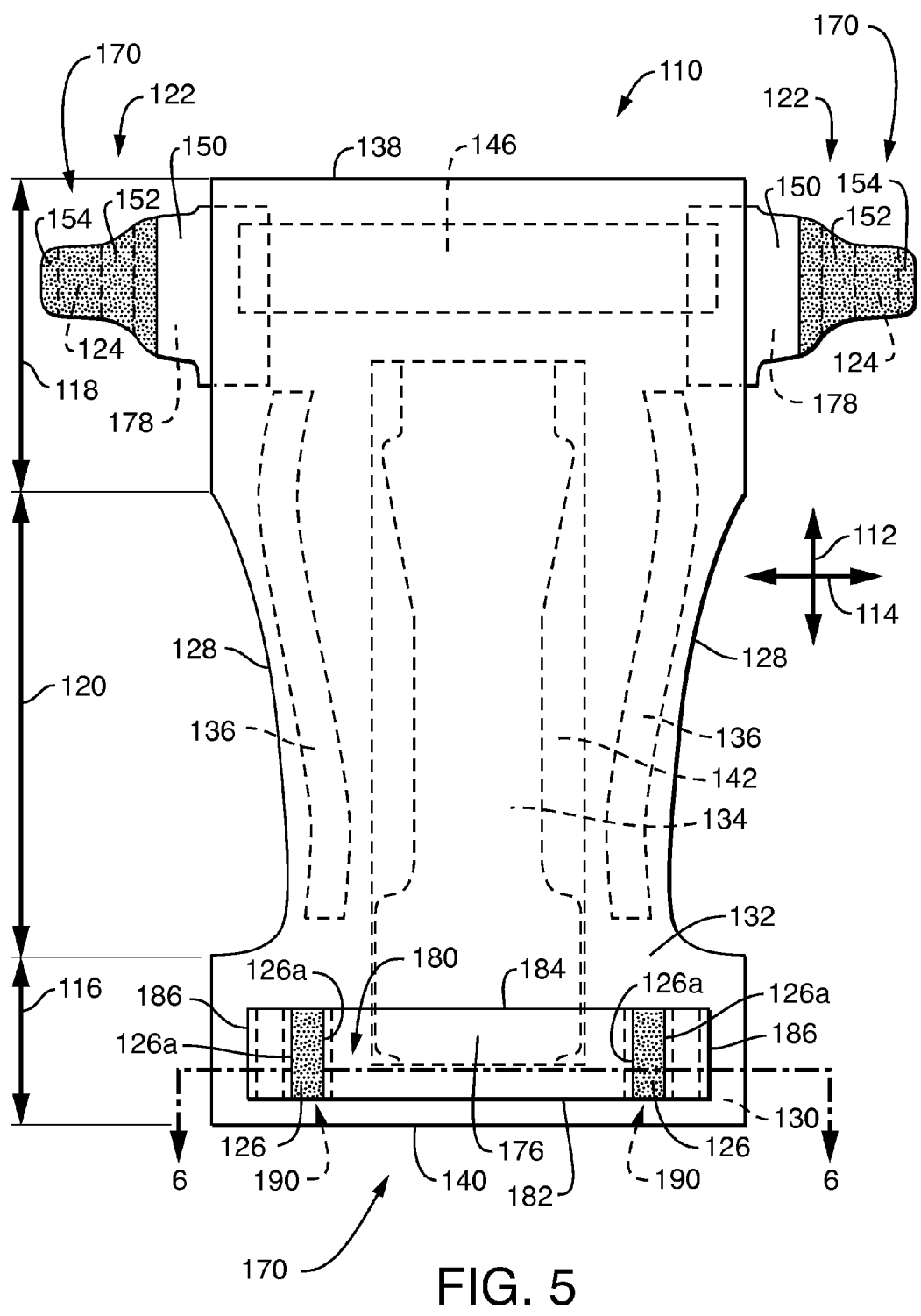
FIG. 5 is a top plan view of an embodiment of a diaper according to the invention, the diaper being in an unfolded and laid flat condition to show an outer surface of the diaper which faces away from the wearer when the diaper is worn.

These features will become more apparent with reference to the accompanying drawings. FIG. 5 illustrates one suitable embodiment of a diaper (broadly, "an absorbent article"), indicated generally at 110, in an unfolded and laid flat condition to show an outer surface of the diaper 110 which faces away from the wearer when the diaper 110 is worn. Some portions of the diaper 110 are illustrated in FIG. 5 and are shown in a dashed line-type to illustrate underlying structures. The diaper 110 has a longitudinal direction 112 and a lateral direction 114. While the present description will be made in the context of a diaper 110, it should be understood that the present disclosure is also applicable to other personal care absorbent articles, such as adult incontinence garments, children's training pants, swim pants, and the like. While the embodiments and illustrations described herein may generally apply to absorbent articles manufactured in the product longitudinal direction, which is hereinafter called the machine direction manufacturing of a product, it should be noted that one of ordinary skill in the art could apply the information herein to absorbent articles manufactured in the latitudinal direction of the product, which hereinafter is called the cross direction manufacturing of a product, without departing from the spirit and scope of the disclosure.

In one suitable embodiment, the diaper 110 is a disposable absorbent article. As used herein, the term "disposable absorbent article" refers to articles which absorb and contain body exudates and which are intended to be discarded after a limited period of use. The articles are not intended to be laundered or otherwise restored for reuse. The articles can be placed against or in proximity to the body of a wearer to absorb and contain various exudates discharged from the body. It is understood that in other suitable embodiments, the diaper 110 can be reusable. That is, the diaper 110 can be intended for multiple uses without departing from some aspects of this disclosure.

In the longitudinal direction 112, the diaper 110 defines a front portion 116, a back portion 118, and a crotch portion 120 extending between and connecting the front portion 116 and the back portion 118. The diaper 110 includes a bodyside liner 130, an outer cover 132, and an absorbent core 134 located between the bodyside liner 130 and the outer cover 132. The bodyside liner 130, outer cover 132 and absorbent core 134 collectively define an absorbent assembly. The absorbent assembly can be any suitable shape including, for example, generally I-shaped as illustrated in FIG. 5, rectangular, trapezoidal, T-shaped, or hourglass shaped. As used herein, reference to the front portion 116 refers to that part of the diaper 110 which is generally located on the front of a wearer when in use. Reference to the back portion 118 refers to the portion of the diaper 110 generally located at the back of the wearer when in use, and reference to the crotch portion 120 refers to that portion which is generally located between the legs of the wearer when in use.

In the illustrated embodiment, the back portion 118 includes a straight back waist edge 138 and the front portion 116 includes a straight front waist edge 140. As used herein, "straight edge" refers to edges that are substantially free from curves, bends, angles, notches, or irregularities. It is understood, however, that the back waist 138 and the front waist 140 may be cut in any suitable shape as are known in the art (e.g., arcuate). As seen in FIG. 5, the diaper 110 has opposite longitudinal side edges 128 that extend between the back waist edge 138 and the front waist edge 140. In the illustrated embodiment, each of the side edges 128 includes an arcuate portion for defining a portion of a leg opening during wear of the diaper 110.

The bodyside liner 130 of the diaper 110, as best shown in FIGS. 6A-6C and 8, defines a body facing surface that is intended to be worn adjacent and in direct contact with the body of the wearer. The bodyside liner 130 can be suitably compliant, soft feeling and nonirritating to the wearer's skin. The bodyside liner 130 can be less hydrophilic than the absorbent core 134 and sufficiently porous to be liquid permeable. The bodyside liner 130 can be manufactured from a wide selection of suitable web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 130 is suitably adapted to isolate the wearer's skin from liquids and moisture held by the absorbent core 134. In some embodiments, the bodyside liner 130 can be coterminous with the outer cover 132 and can extend from the rear waist edge 138 to the front waist edge 140 and from longitudinal side edge 128 to the opposite longitudinal side edge 128. In other embodiments, the bodyside liner 30 can be narrower than the outer cover 132 in the lateral direction 114 and/or shorter than the outer cover 132 in the longitudinal direction 112.

The outer cover 132 of the diaper 110, which is illustrated in FIG. 5, defines a garment facing surface which is intended to be worn adjacent the clothing of the wearer. In one suitable embodiment, the outer cover 132 is a polyethylene film. In another suitable embodiment, the outer cover 132 comprises a woven or non-woven fibrous web layer which has been totally or partially constructed or treated to impart a desired level of liquid impermeability to selected regions of the outer cover that are adjacent or proximate the absorbent core 134. For example, a clothlike outer cover may be composed of polypropylene spunbond fabric which is laminated and thermally bonded to a stretch-thinned polypropylene film. The outer cover 132 may include a microporous, "breathable" material which permits vapors to escape from diaper 110 while still preventing liquid exudates from passing through. For example, the outer cover 132 may be composed of a microporous polymer film or a nonwoven fabric which has been coated or otherwise treated to impart a desired level of liquid impermeability. The outer cover 132 can also be a multilayered structure including a film layer and a woven or non-woven fibrous web layer. The outer cover 132 can also be embossed or otherwise provided with a matte finish to exhibit a more aesthetically pleasing appearance.

The bodyside liner 130 and the outer cover 132 are generally joined in facing relationship with the absorbent core 134 located therebetween. The bodyside liner 130 and the outer cover 132 can be joined to each other around the outer periphery of the diaper 110 by any means known to those skilled in the art such as adhesive bonds, ultrasonic bonds, thermal bonds, and the like, and combinations thereof. As used herein, the term "join" or "couple", and derivatives thereof, encompass configurations wherein an element is directly secured to the other element by affixing the element directly to the other element, and configurations wherein the element is indirectly secured to the other element by affixing the element to intermediate member(s) which in turn are affixed to the other element.

As mentioned above, the absorbent core 134 is positioned between the bodyside liner 130 and the outer cover 132. The absorbent core 134 is generally conformable and capable of absorbing and retaining liquid body exudates. The absorbent core 134 can include superabsorbent material, staple fibers, binder fibers, and the like, and combinations thereof as is known in the art. The absorbent core 134 may have any of a number of shapes and sizes. For example, the composite absorbent core 134 may be rectangular, I-shaped, or T-shaped. The absorbent core 134 can have a length and a width that can be less than or equal to the length and width of the diaper 110. The size and absorbent capacity of the absorbent core 134 should be compatible with the size of the intended wearer and the fluid loading imparted by the intended use of the diaper 110.

In one suitable embodiment, the diaper 110 may include a surge portion (not shown) disposed between the absorbent core 134 and the bodyside liner 130. The surge portion serves to quickly collect and temporarily hold liquids discharged by the wearer and then release the liquids to the absorbent core 134. Various woven and nonwoven materials can be used to construct the surge portion. For example, the surge portion may be a layer of a spunbonded or meltblown web of polyolefin fibers. The surge portion may also be a bonded carded web of natural and synthetic fibers. The surge portion may be a substantially hydrophobic material and, optionally, can be treated with a surfactant or otherwise to impart a desired level of wettability and hydrophilicity.

In some embodiments, the diaper 110 can include a fluid transfer layer 142. The fluid transfer layer 142 can be disposed between the absorbent core 134 and the bodyside liner 130. In some embodiments, the fluid transfer layer 142 can be in contact with and at least partially wrap the absorbent core 134. The fluid transfer layer 142 can be pliable, less hydrophilic than the absorbent core 134, and sufficiently porous to thereby permit liquid body exudates to penetrate through the fluid transfer layer 142 to reach the absorbent core 134. In an embodiment, the fluid transfer layer 142 can have sufficient structural integrity to withstand wetting thereof and of the absorbent core 134. The fluid transfer layer 142 can be a single layer of material or a laminate constructed from two or more layers. The fluid transfer layer 142 can include, but is not limited to natural and synthetic fibers such as polyester, polypropylene, acetate, nylon, polymeric materials, and cellulosic materials, and mixtures thereof. In some embodiments, the fluid transfer layer 142 can include spunbond and/or meltblown materials. The fluid transfer layer 142 can have a longitudinal length the same as, greater than, or less than the longitudinal length of the absorbent core 134.

The diaper 110 includes a pair of elasticized, longitudinally-extending leg cuffs 136. The leg cuffs 136 are adapted to fit about the legs of a wearer in use and serve as a mechanical barrier to the lateral flow of body exudates. In one suitable embodiment, the leg cuffs 136 can be formed by portions of the outer cover 132, and/or bodyside liner 130, which extend beyond the longitudinal sides of the absorbent core 134. In another suitable embodiment, the leg cuffs 136 can be formed from separate materials (e.g., strands of leg elastics) joined to the outer cover 132 and/or the bodyside liner 130.

The diaper 110 may further include a front waist elastic (not shown) and/or a back waist elastic 146. In the illustrated embodiment, for example, the diaper 110 has a back waist elastic 146 but not a front waist elastic. The back waist elastic 146 is arranged to draw and hold the diaper 110 against the wearer, particularly against the waist of the wearer, as will be more fully discussed.

Figure 1:
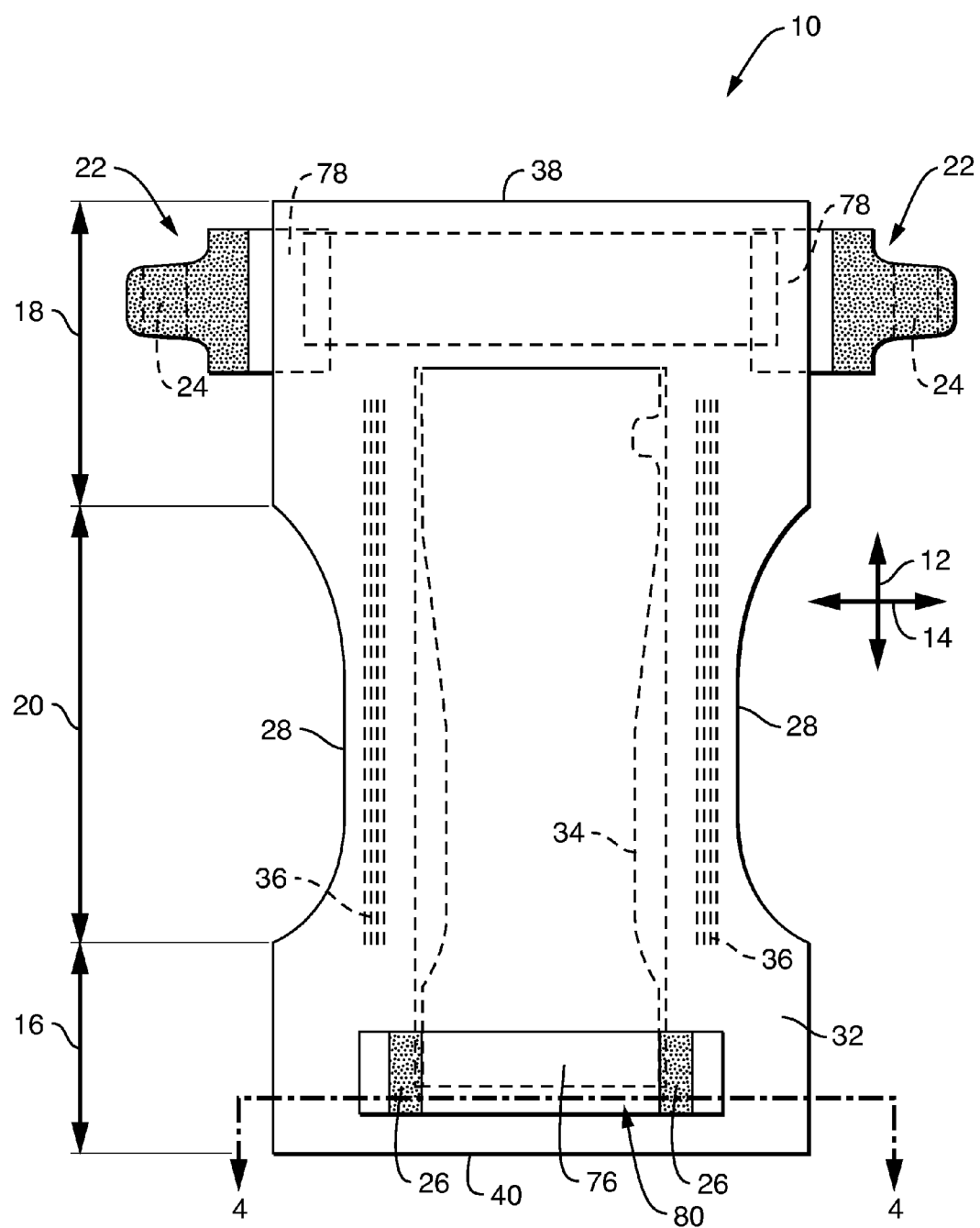
FIG. 1 is a top plan view of a known diaper in an unfolded and laid flat condition to show an outer surface of the diaper which faces away from the wearer when the diaper is worn.
Figure 7:
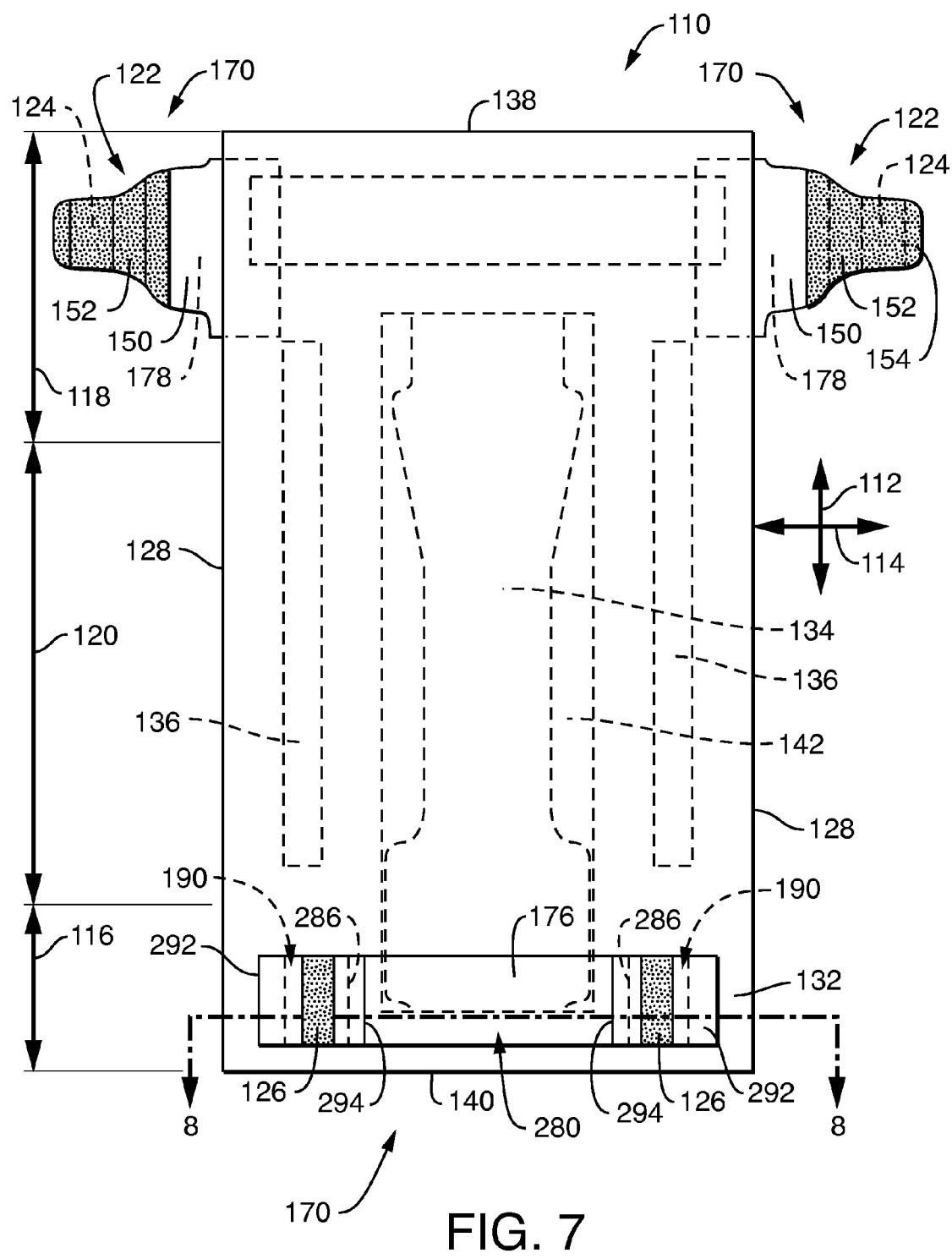
FIG. 7 is a top plan view of an alternative embodiment of a diaper according to the invention, the diaper being in an unfolded and laid flat condition to show an outer surface of the diaper which faces away from the wearer when the diaper is worn.

Materials suitable for use in forming leg cuffs 136 and/or waist elastics 146 are known to those skilled in the art. Examples of such materials are strands or ribbons of a polymeric, elastomeric material which are adhered to the diaper 110 in a stretched position, or which are attached to the diaper 110 while the diaper is pleated, such that elastic constrictive forces are imparted to the diaper 110. The leg cuffs 136 and/or waist elastics 146 may have any configuration which provides the desired performance. The leg cuffs 136 may be generally straight (as illustrated in FIGS. 1 and 7) or optionally curved (as illustrated in FIG. 5) to more closely fit the contours of the legs of the wearer. As used herein, "elastic," "elastomeric," and the like refer to the ability of a material or composite to be elongated by at least about 50 percent and upon relaxation to return to within at least 50 percent of its original length.

The leg cuffs 136 and/or waist elastics 146 may be attached to the diaper 110 in any way known to those skilled in the art. For example, the leg cuffs 136 and/or waist elastics 146 may be joined to the diaper 110 by ultrasonic bonding, thermal bonding, adhesive bonding, and the like, and combinations thereof.

The diaper 110 may also include a pair of containment flaps 148 (as best shown in FIGS. 6A-6C and FIG. 8) that extend longitudinally along the diaper 110 and are adapted to provide a barrier to the lateral flow of body exudates. The containment flaps 148 can be connected to the bodyside liner 130 or other components as is well known in the art and can include a base 147 and a stem 149, as will be discussed in further detail below. The base 147 of each containment flap 148 can extend to the respective longitudinal side edges 128 of the diaper 110, as shown, however, it is contemplated that the base 147 of each containment flap 148 can be configured such that the base 147 of each containment flap 148 does not extend to the respective longitudinal side edges 128 of the diaper 110. Suitable configurations of the containment flaps 148 are described, for example, in U.S. Pat. No. 5,599,338 issued Feb. 4, 1997, to K. Enloe, the entirety of which is incorporated herein by reference.

As seen in FIG. 5, the back portion 118 of the diaper includes a pair of back or rear ears, indicated generally at 122. In one suitable embodiment, the back ears 122 can be formed from extensions of the bodyside liner 130, the outer cover 132, or combinations of both the bodyside liner 130 and the outer cover 132. In another suitable embodiment, and as illustrated in FIGS. 5 and 7, the back ears 122 can be formed as separate components and attached to the bodyside liner 130, the outer cover 132, or both the bodyside liner 130 and the outer cover 132 as is known in the art. In the illustrated embodiment, the back ears 122 are attached to the body-facing surface of the bodyside liner 130 such that the attached portion of the ears 122 are disposed between the wearer's body and bodyside liner 130 when the diaper 110 is worn.

In one suitable embodiment, each of the back ears 122 includes an elastomeric portion 150, a non-elastomeric portion 152, and a primary first fastening component 124 mounted to the non-elastomeric portion (as shown in FIG. 5). A portion of the elastomeric portion 150 overlaps the bodyside liner 130. The part of each of the elastomeric portions 150 overlapping the bodyside liner 130 is bonded (e.g., adhesive bonding, thermal bonding, both thermal and adhesive bonding) to at least the bodyside liner 130. In another suitable embodiment, the elastic component 150 may be eliminated and the entire back ear 122 may be constructed from the non-elastic component 152. The elastomeric portion 50 of the back ears 122 can be shaped to be non-rectangular, such as shown in FIGS. 5 and 7, or can be rectangular, such as shown in FIG. 1, or can be any other suitable shape.

The elastomeric portions 150 of the back ears 122 can be formed from any type of elastomeric material capable of performing as described herein. In one suitable embodiment, the elastomeric material will be stretchable in at least one direction (e.g., in the lateral direction 114 of the diaper 110 as viewed in FIG. 5) and alternatively, the elastomeric material will be stretchable in two directions (e.g., in both the longitudinal direction 112 and the lateral direction 114 of the diaper 110 as viewed in FIG. 5). Suitably when the elastomeric material is stretchable in a single direction, the stretch direction of the elastomeric material will be oriented so as to provide elastomeric forces which tend to pull the front and rear portions 116, 118 of the article towards one another such that the article is maintained about the waist of a wearer.

In one suitable embodiment, the elastomeric material from which the elastomeric portions 150 of the back ears 122 are formed is capable of being elongated by at least about 50 percent, alternatively by at least about 100 percent, alternatively by at least about 130 percent. After elongation to 50 percent (if the elastomeric material is capable of being elongated to no more than 100 percent) or 100 percent (if the elastomeric material is capable of being elongated to more than 100 percent), the elastomeric material suitably recovers to at least about 50 percent of its original length, alternatively to at least about 80 percent of its original length. The elastomeric material may be an inherently elastomeric material, that is, one which is formed in an elastomeric state, or may be rendered elastomeric through processing subsequent formation. For example, the elastomeric material may be heat or pressure activated. The elastomeric portions 150 of the back ears 122 can be formed from a stretch-bonded-laminate (SBL) material, a neck-bonded-laminate (NBL) material, an elastomeric film, an elastomeric foam material, or the like.

Each of the non-elastomeric portions 152 of the back ears 122 is attached to a respective one of the elastomeric portions 150, and the primary first fastening components 124 (such as a hook material) are in turn disposed on the non-elastomeric portions 152. As illustrated in FIG. 5, the non-elastomeric portions 152 of the back ears 122 extend in part transversely outward of the respective elastomeric portion 150 and the primary first fastening component 124 of each of the non-elastomeric portions 152 is configured for engaging a loop component disposed in the front waist region 116 of the diaper 110 in the wear configuration, as will be discussed more fully.

As seen best in FIG. 5, each of the illustrated non-elastomeric portions 152 further comprise a grip region 154 transversely outward of the primary first fastening component 124 for use in manually gripping and manipulating the non-elastomeric portion 152 and more broadly the respective back ear 122 relative to the diaper 110. The grip region 154 is non-attachable to the diaper 110. The term "non-attachable" as used in this instance means that the grip region 154 is not releasably or otherwise removably attachable to the diaper 110. In one embodiment, the grip region 154 extends transversely outward from the respective primary first fastening component 124 a distance of at least about 1 mm, such as in the range of about 1 mm to about 10 mm to provide sufficient unattached material for readily gripping and pulling on the non-elastomeric portion 152.

Figure 2:
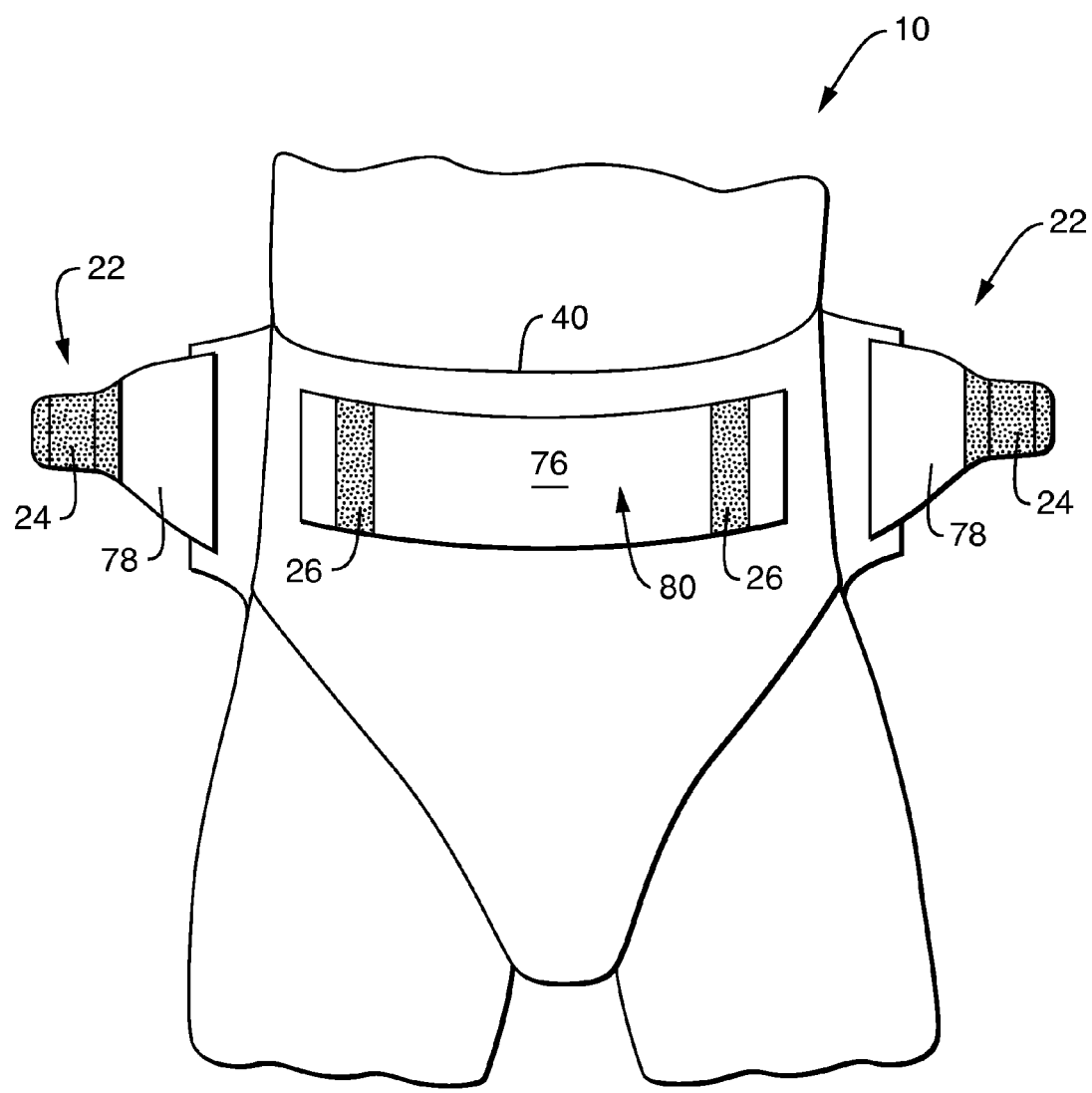
FIG. 2 is a front view of the diaper of FIG. 1 in a wear configuration with the fastening system not fastened.
Figure 3:
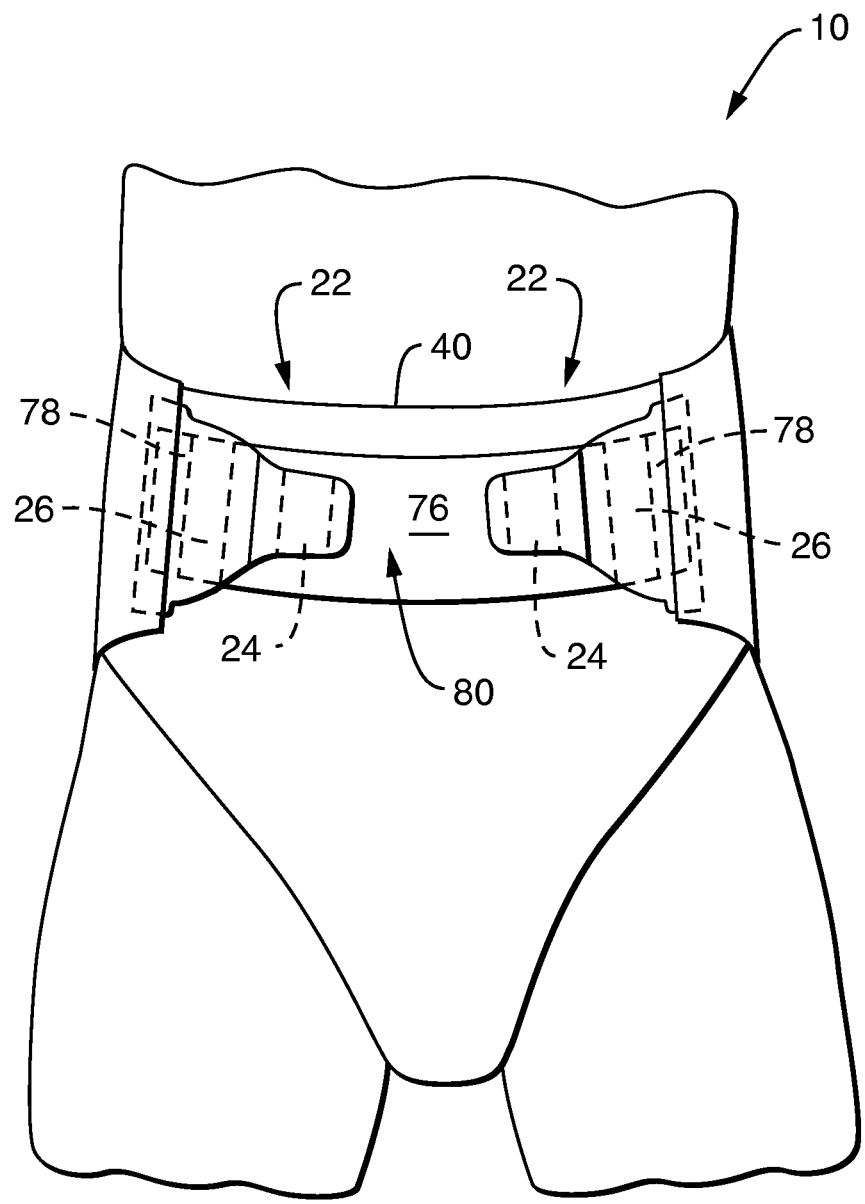
FIG. 3 is a front view of the diaper of FIG. 2 in a wear configuration with the fastening system fastened.

Just as shown for the diaper 10 of FIGS. 1-4, the diaper 110 of FIGS. 5-8 can be selectively moved from the unfastened configuration (such as illustrated in FIG. 2 for diaper 10) to a fastened or wear configuration (such as illustrated in FIG. 3 for diaper 10) by attaching the back waist region 118 (and more specifically the back ears 122) to the front waist region 116 using an article fastening system 170 to define a three-dimensional wear configuration of the diaper 110 having a waist opening and a pair of leg openings. The diaper 110 can be configured such that the back waist region 118 (and more specifically the back ears 122) overlap the front waist region 116 upon connection thereto (such as shown for diaper 10 in FIG. 3), which is convenient. However, the diaper 110 can also be configured so that the front waist region 116 overlaps the back waist region 118 when connected.

According to some embodiments, the article fastening system 170 comprises a primary fastening system and a secondary fastening system. The primary fastening system comprises the primary first fastening components 124 disposed on the non-elastomeric portions 152 of the back ears 122 and at least one corresponding primary second fastening component 176 which is adapted for refastenable engagement to the primary first fastening components 124. In one suitable embodiment, an outer surface of each of the primary fastening components 124, 176 comprises a plurality of engaging elements. More specifically, the engaging elements of the primary first fastening components 124 are adapted to repeatedly engage and disengage corresponding engaging elements of the primary second fastening components 176 to releasably secure the diaper 110 in its wear configuration.

The primary fastening components 124, 176 may comprise any refastenable fasteners suitable for absorbent articles, such as adhesive fasteners, cohesive fasteners, mechanical fasteners, or the like. In one suitable embodiment, the primary fastening components 124, 176 comprise mechanical fastening components, such as hook and loop fasteners. For example, suitable hook and loop components can be provided by interlocking geometric shaped materials. As used herein, "hook" broadly refers to any suitable mechanical fastener adapted to engage loop components including, e.g., hooks, bulbs, mushrooms, arrowheads, balls on stems, stems, structures having stems that engage foam such as open cell foam or the like, etc. Other suitable mechanical fastening components include male and/or female mating components, buckles, snaps, or the like. In the illustrated embodiment, the primary first fastening components 124 comprise hook fasteners and the primary second fastening components 176 comprise a complementary loop fastener disposed on the outer surface of the outer cover 132. Alternatively, the primary first fastening components 124 may comprise loop fasteners and the primary second fastening components 176 may comprise complementary hook fasteners.

The shape, density, and polymer composition of the hooks and loops may be selected to obtain the desired level of engagement between the primary fastening components 124, 176. A more aggressive hook material may comprise a material with a greater average hook height and/or a greater percentage of directionally-aligned hooks.

In some embodiments, the outer facing surface of the outer cover 132 of the diaper 110 is suitably constructed to define the primary second fastening component 176, which is a loop fastener. That is, the outer cover 132 itself can be formed of a material that defines the primary second fastening component 176 (e.g., vertical filament laminate (VFL) or other suitable material).

In another suitable embodiment, and as illustrated in FIG. 5, the primary second fastening component 176 can be formed as a separate component and attached to the outer surface of the diaper's outer cover 132. More specifically, a strip, indicated generally at 180, comprising loop fastening material is attached to the front waist region 116 of the diaper. The strip 180 comprises an upper edge 182, a lower edge 184, and a pair of side edges 186 connecting the upper and lower edges 182, 184. The upper edge 182 is spaced from the front waist edge 140 and the side edges 186 are spaced from the respective side edges 128 of the diaper 110.

The secondary fastening system of the article fastening system 170 comprises secondary first fastening components 126 and secondary second fastening components 178. For purposes of clarity, the secondary first fastening component 126 and the secondary second fastening component 178 on the left side of FIG. 5 can be referred to as a left secondary first fastening component 126 and a left secondary second fastening component 178, respectively, while the secondary first fastening component 126 and the secondary second fastening component 178 on the right side of FIG. 5 can be referred to as a right secondary first fastening component 126 and a right secondary second fastening component 178. The secondary first fastening components 126 are disposed on the front portion 116 of the diaper 110 and are adapted for refastenable engagement to at least one corresponding secondary second fastening component 178 (e.g., the elastomeric portion 150 of the back ears 122). As illustrated in FIG. 5, in some embodiments, the strip 180 may comprise the pair of spaced-apart secondary first fastening components 126. As such, the strip 180 can serve as a carrier material for the secondary first fastening components 126.

In the illustrated embodiment of FIG. 5, the secondary first fastening components 126 comprise hook fasteners and are configured to engage the secondary second fastening components 178 in the wear configuration of the diaper 110. Again, as used herein "hook" fasteners refers broadly to any suitable mechanical fastener adapted to engage loop components including, e.g., hooks, bulbs, mushrooms, arrowheads, balls on stems, stems, structures having stems that engage foam such as open cell foam or the like, etc. In one embodiment, the secondary first fastening components 126 may be constructed of polyethylene, polypropylene, or other suitable polymer blends. In one suitable embodiment, the elastomeric portions 150 of the back ears 122 are constructed so at least the inner surfaces of the elastomeric portions define the secondary second fastening components 178 in the form of loop fastening components (i.e., the elastomeric portions and the respective secondary second fastening components are formed integrally). The elastomeric portions 150 in one suitable embodiment can be constructed of NBL material so that each elastomeric portion 150 itself defines a loop fastening component. In another suitable embodiment, the elastomeric portions 150 can be constructed of VFL material so that each elastomeric portion 150 itself defines a loop fastening component. It is understood, however, that the secondary second fastening components 178 may be formed separate from the elastomeric portions 150 and attached thereto, such as by adhesive, thermal bonds, ultrasonic bonds, pressure bonds, or other suitable techniques without departing from the scope of this disclosure.

In other suitable embodiments, the secondary first fastening components 126 may comprise loop fasteners and the secondary second fastening components 178 may comprise hook fasteners. Further, in some embodiments the secondary first fastening components 126 may be a single, integral fastener. For example, in one suitable embodiment the secondary first fastening components 126 may be a single, hook fastener, and the secondary second fastening components 178 may be loop fasteners.

In one suitable embodiment, the strip 180 can comprise both the secondary first fastening components 126 and the primary second fastening component 176. In one such embodiment where the primary second fastening component 176 comprises a loop material and the secondary first fastening component 126 comprises a hook material, the strip 180 may be a suitable loop material (forming the primary second fastening component), and then the hook material may be extruded onto the loop material at two or more locations forming the secondary first fastening components 126. As such, the strip 180 can serve as a carrier material for the secondary first fastening components 126.

In another suitable embodiment, the secondary first fastening components 126 can be formed separate from the primary second fastening component 176. In such an embodiment, the primary second fastening component 176 can be formed to define the strip 180 and the secondary first fastening components 126 can be attached in overlaying relationship with portions of the primary second fastening component. In such embodiments, the secondary first fastening components 126 may be attached to the strip 180 and/or the primary second fastening component 176 using any suitable means known to those skilled in the art, including, e.g., adhesive bonds, ultrasonic bonds, thermal bonds, pressure bonds, and the like, and combinations thereof. In such a configuration, the strip 180 can serve as a carrier material for the secondary first fastening components 126.

In some embodiments, the secondary first fastening components 126 may be attached to the diaper 110 and/or the strip 180 after the strip has been attached to the diaper 110. For example, in one suitable embodiment the strip 180 may be first bonded to the diaper 110 using any suitable means as discussed, and then the secondary first fastening components 126 may be bonded to or extruded on the strip 180. In other embodiments, the strip 180 comprising both the secondary first fastening components 126 and primary second fastening components 176 can be attached to the diaper 110 as one single unit.

According to some embodiments, the secondary first fastening components 126 and/or the strip 180 may be sufficiently bonded to the diaper 110 such that a shear force exerted on the secondary first fastening components 126 and/or the strip 180 during use of the diaper 110 does not cause the secondary first fastening components 126 and/or the strip 180 to loosen or completely disengage from the diaper 110. For example, in some embodiments an improved adhesive or the like can be used such that the secondary first fastening components 126 and/or the strip 180 remain securely fastened to, e.g., the outer cover 132 despite the forces exerted on the fastening system 170 during use. In such embodiments, the diaper 110 may be less prone to pop-opens and the edges of the secondary first fastening components 126 and/or the strip 180 may remain flush with the outer cover 132 thus reducing irritation during wear which may otherwise be caused by a loose secondary first fastener 126 and/or a loose strip 180.

When the diaper 110 is moved to the wear configuration (similar to that as shown for the diaper 10 in FIG. 3) with the primary fastening components 124, 176 engaging one another, the secondary fastening components 126, 178 may also engage one another in order to provide increased stability and leakage protection. For example, because the article fastening system 170 comprises four engagement points, the diaper 110 will be less prone to pop-opens when worn. Further, because the secondary fastening components 126, 178 engage each other closer to a side of a wearer than an engagement point of the primary fastening components 124, 176, the secondary fastening system secures the diaper 110 nearer the wearer's sides and legs thus reducing leakage near the leg openings of the diaper 110. Still further, and again because the secondary fastening components 126, 178 engage each other near a side of the wearer, the secondary fastening system may provide increased stability, thus reducing the occurrence of, e.g., sagging of the diaper 110 due to movement of the wearer.

Referring back to FIGS. 1-4, while the diaper 10 of the prior art that includes a fastening system with secondary first fastening components 26 and secondary second fastening components 78 provides beneficial properties, the diaper 10 may also provide unintended effects of increasing the rigidity of the front portion 16 of the diaper 10. In turn, this increased rigidity in the front portion 16 of the diaper 10 can increase the potential for red-marking or discomfort to the wearer in the area of the secondary first fastening components 26, as compared to a diaper that does not have secondary first fastening components 26.

Figure 4:
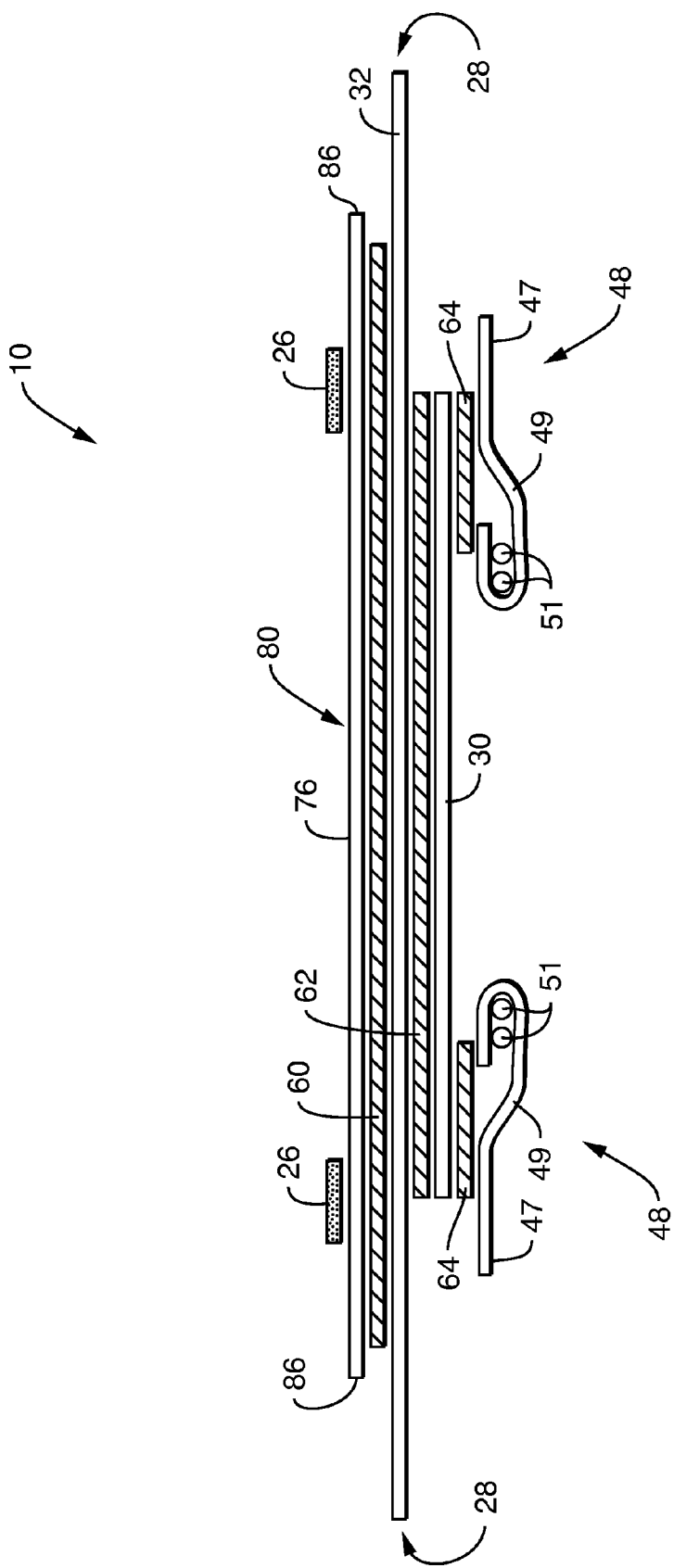
FIG. 4 is a cross-sectional view of the diaper of FIG. 1 taken along line 4-4.

Turning now to FIG. 4, an exemplary cross-section of the diaper 10 along line 4-4 from FIG. 1 is shown in an exploded view. The diaper 10 includes secondary first fastening components 26 positioned on strip 80, as well as the outer cover 32 and the bodyside liner 30. The diaper 10 also includes a pair of containment flaps 48, which each include a base 47 and a stem 49. As is known in the art, the containment flaps 48 can include strands of elastic 51. As is common in prior art diapers 10, the strip 80 forming the primary second fastening component 76 and including the secondary first fastening components 26, is joined to the outer cover 32 with adhesive 60. The adhesive 60 can be applied via spray, slot-coat, or in any suitable fashion. As is shown in FIG. 4, the adhesive 60 can extend almost an entire lateral width of the strip 80, substantially from side edge 86 to side edge 86 of the strip 80. Additionally, an adhesive 62 is also used to join outer cover 32 to the bodyside liner 30. An adhesive 64 is also employed to join each of the containment flaps 48 to the bodyside liner 30. As illustrated in FIG. 4, the adhesive 64 can couple at least a portion of the stem 49 of each containment flap 48 to the bodyside liner 30 as well as couple at least a portion of the base 47 of each containment flap 48 to the bodyside liner 30. As is known in the art, the stems 49 of the containment flaps 48 are generally only coupled to the bodyside liner 30 in a portion of the front and rear portions 16, 18 of the diaper 10, and extend away from the bodyside liner 30 in the crotch region 20 of the diaper 10 to provide a gasket against the wearer's skin in the crotch region 20.

Turning to the diaper 110 of the present disclosure, reference is now made to FIGS. 5 and 6A-6C. As shown in FIG. 5, diaper 110 includes a region of flexibility 190 under each of the secondary first fastening components 126. The diaper 110 can include one or more regions of flexibility 190 under a secondary first fastening component 126 that provide the secondary fastening system with improved flexibility. As will be discussed in further detail below, a region of flexibility 190 can provide relative movement between adjacent components of the diaper 110 in an area of the diaper 110 under a secondary first fastening component 126. In some embodiments, a region of flexibility 190 can be provided between adjacent components of the diaper 110 between a secondary first fastening component 126 and the bodyside liner 130 in an area under the secondary first fastening component 126.

Figure 6A:
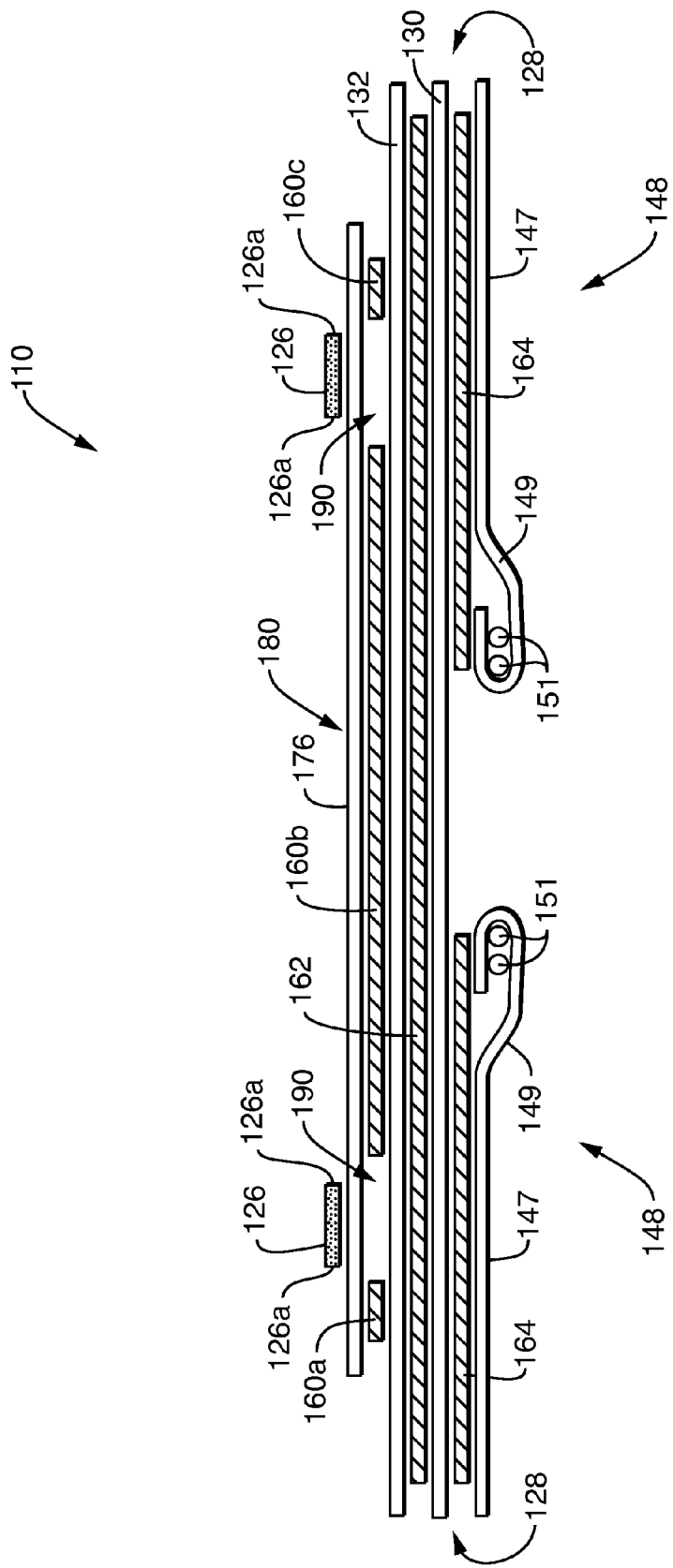
FIG. 6A is a cross-sectional view of the diaper of FIG. 5 taken along line 6-6 showing a first configuration of coupling components of the diaper under the secondary first fastening components.

For example, FIG. 6A provides a cross-sectional, exploded view taken along line 6-6 to illustrate one embodiment of a region of flexibility 190 under the secondary first fastening components 126. Secondary first fastening components 126 are coupled to the strip 180, which forms the primary second fastening component 176 of the article fastening system 170. Adhesives 160a, 160b, 160c couple the strip 180 to the outer cover 132 of the diaper 110 in the depicted embodiment. In another embodiment, the strip 180 can be coupled to the outer cover 132 of the diaper 110 with adhesive 160b, but without adhesives 160a and 160c. An adhesive 162 couples the outer cover 132 to the bodyside liner 130. The adhesive 162 can extend substantially from one longitudinal side edge 128 to the opposite longitudinal side edge 128 of the diaper 110. Additionally, an adhesive 164 couples the bodyside liner 130 to each of the containment flaps 148. As shown in the embodiment depicted in FIG. 6A, the adhesive 164 can couple at least a portion of the base 147 and at least a portion of the stem 149 of each containment flap 148 to the bodyside liner 130. In other embodiments, the adhesive 164 need not couple the stem 149 to the bodyside liner 130.

Notably, the areas where adhesives 160a, 160b, and 160c are not present between the strip 180 and the outer cover 132 are under the secondary first fastening components 126. As used herein, the term "under" describes the relative position of components of a diaper 110 in the context of a top plan view of the diaper 110 in a laid-flat configuration in which the outer cover 132 is facing outwards towards the viewer, such as the configuration of the diaper 110 shown in FIG. 5. The absence of adhesive between adhesives 160a and 160b and the absence of adhesive between adhesives 160b and 160c provide for a region of flexibility 190 under each of the secondary first fastening components 126 in the embodiment depicted in FIG. 6A. While the strip 180 as a whole is coupled to the outer cover 132, the regions of flexibility 190 each provide for at least a portion of an area of the strip 180 under each of the secondary first fastening components 126 that is not coupled to the outer cover 132. As a result, the strip 180 in the regions of flexibility 190 can move relative to the outer cover 132, and as such, the secondary first fastening components 126 can move relative to the outer cover 132. Such relative movement between the secondary first fastening components 126 and the outer cover 132 can provide flexibility of the secondary fastening system when the wearer makes a movement (e.g., walks, crawls, runs, bends, etc.) that affects or binds the front portion 116 of the diaper 110. In doing so, the secondary first fastening components 126 provide increased pliability of the diaper 110, reducing the potential for red-marking or discomfort to the wearer in the area of the secondary first fastening components 126. Additionally, the flexibility of the secondary first fastening components 126 with respect to the outer cover 132 may also decrease the likelihood of a pop-open (i.e., the secondary first fastening component 126 becoming disengaged from the secondary second fastening component 178).

It is to be noted that although FIGS. 5 and 6A depict that the area of the strip 180 under the secondary first fastening components 126 that is not coupled to the outer cover 132 extends beyond the longitudinal sides 126a of each of the secondary first fastening components 126 and for the entire length of the secondary first fastening components 126 in the longitudinal direction 112, such a configuration, while preferred, is not required by this disclosure. Rather, other configurations are contemplated, including, but not limited to, a configuration where only a portion of the area of the strip 180 under the secondary first fastening components 126 is not coupled to the outer cover 132.

FIG. 6B provides another cross-sectional, exploded view taken along line 6-6 of FIG. 5, similar to FIG. 6A, but illustrates an alternative exemplary configuration of a diaper 110 providing a region of flexibility 190 under the secondary first fastening components 126. In FIG. 6B, an adhesive 160 couples the strip 180 to the outer cover 32 and extends almost an entire lateral width of the strip 180, substantially from side edge 186 to side edge 186 of the strip 180. Adhesives 162a, 162b, and 162c couple the outer cover 132 to the bodyside liner 130 in the depicted embodiment. In another embodiment, the outer cover 132 can be coupled to the bodyside liner 130 of the diaper 110 with adhesive 162b, but without adhesives 162a and 162c. Additionally, an adhesive 164 couples the bodyside liner 130 to each of the containment flaps 148. As shown in the embodiment depicted in FIG. 6B, the adhesive 164 can couple at least a portion of the base 147 and at least a portion of the stem 149 of each containment flap 148 to the bodyside liner 130, such as previously discussed above with respect to the diaper 110 depicted in FIG. 6A. In other embodiments, the adhesive 164 need not couple the stem 149 to the bodyside liner 130. As shown in FIG. 6B, the base 147 of each containment flap 148 need not extend to the respective longitudinal edge 128 of the diaper 110.

As shown in FIG. 6B, adhesives 162a, 162b, and 162c are not present between the outer cover 132 and the bodyside liner 130 at a position under the secondary first fastening components 126. Thus, the absence of adhesives 162a, 162b, and 162c for at least a portion of an area under each of the secondary first fastening components 126 provides for a region of flexibility 190 under each of the secondary first fastening components 126 where the outer cover 132 is not coupled to the bodyside liner 130. As a result, the outer cover 132 in the regions of flexibility 190 can move relative to the bodyside liner 130. Because the secondary first fastening components 126 are indirectly coupled to the outer cover 132 via the strip 180, the secondary first fastening components 126 can move relative to the bodyside liner 130 as well. Similar to the discussion above with respect to FIG. 6A, this relative movement between the secondary first fastening components 126 and the bodyside liner 130 can provide flexibility of the secondary fastening system when the wearer makes a movement (e.g., walks, crawls, runs, bends, etc.) that affects or binds the front portion 116 of the diaper 110. As such, the diaper 110 as illustrated in FIG. 6B can provide benefits of reducing the potential for red-marking and discomfort to a wearer in the area of the secondary first fastening components 126 as well as reduce the potential of pop-opens at the secondary first fastening components 126 (i.e., the secondary first fastening component 126 becoming disengaged from the secondary second fastening component 178).

Of course, the regions of flexibility 190 between the outer cover 132 and the bodyside liner 130 under the secondary first fastening components 126 can change in shape and size from the shapes and sizes as shown herein. For example, while it is preferred to have the area of the outer cover 132 under the secondary first fastening components 126 that is not coupled to the bodyside liner 130 extend beyond the longitudinal sides 126a of each of the secondary first fastening components 126 and extend for the entire length of the secondary first fastening components 126 in the longitudinal direction 112, other configurations are contemplated and still provide the aforementioned benefits. For example, one such non-limiting configuration includes where only a portion of the area of the outer cover 132 under the secondary first fastening components 126 is not coupled to the bodyside liner 130.

Figure 6C:
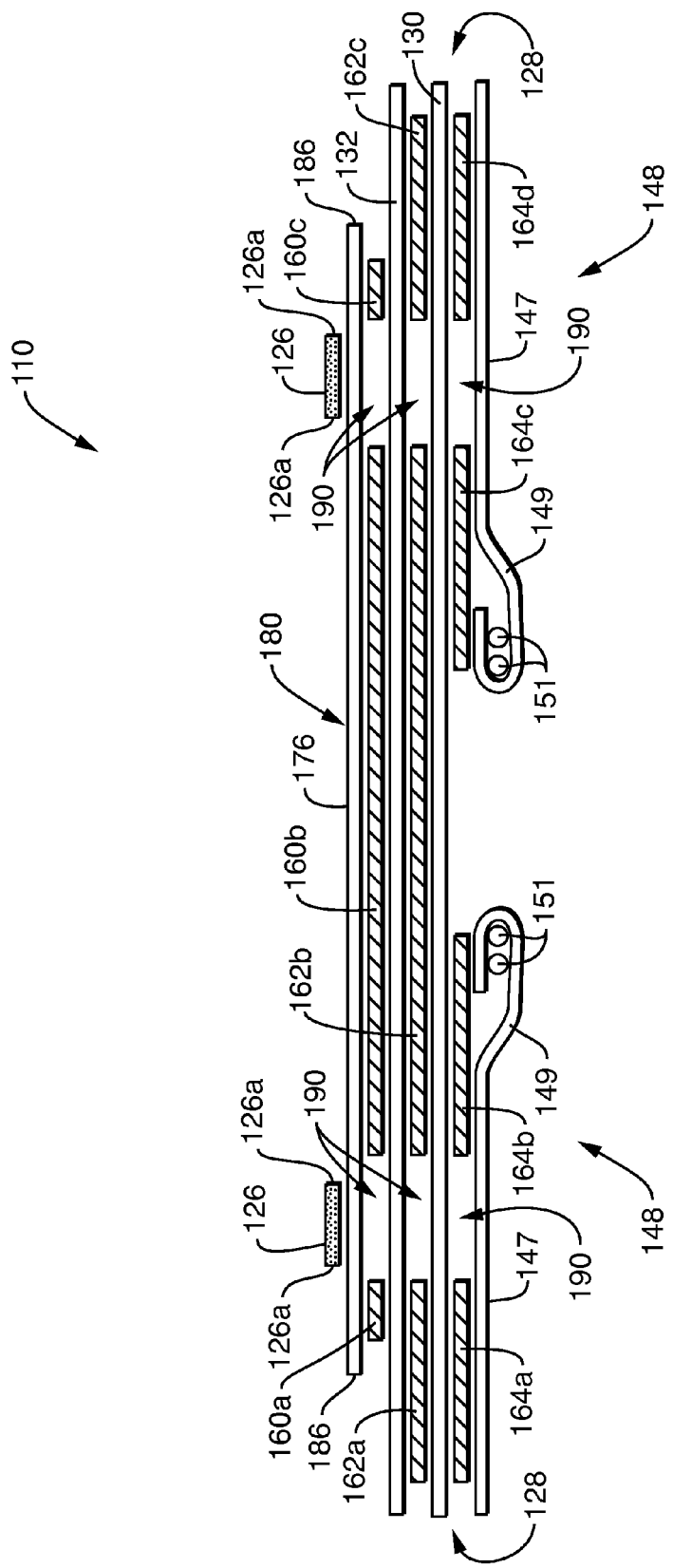
FIG. 6C is a cross-sectional view of the diaper of FIG. 5 taken along line 6-6 showing a third configuration of coupling components of the diaper under the secondary first fastening components.

FIG. 6C illustrates yet another alternative configuration and provides a cross-sectional, exploded view of the diaper 110 taken along line 6-6 from FIG. 5. In FIG. 6C, the strip 180 is coupled to the outer cover 132 with adhesives 160a, 160b, and 160c. The outer cover 132 is coupled to the bodyside liner 130 with adhesives 162a, 162b, and 162c. The bodyside liner 130 is coupled to the containment flaps 148 with adhesives 164a, 164b, 164c, and 164d in the embodiment depicted. Specifically, adhesives 164a, 164b, 164c, and 164d can couple at least a portion of the base 147 and at least a portion of the stem 149 to the bodyside liner 130. As previously discussed, in other embodiments, the adhesive 164 need not couple the stem 149 to the bodyside liner 130. Furthermore, in another embodiment, the bodyside liner 130 can be coupled to the containment flaps 148 of the diaper 110 with adhesives 164b and 164c, but without adhesives 164a and 160d. As can be seen in FIG. 6C, three regions of flexibility 190 are under each of the secondary first fastening components 126.

Regions of flexibility 190 are provided between the strip 180 and the outer cover 132 where there is an absence of adhesive between adhesives 160a and 160b and an absence of adhesive between adhesive 160b and 160c. This area under the secondary first fastening components 126 in which the strip 180 is not coupled to the outer cover 132 provides for relative movement of the secondary first fastening components 126 with respect to the outer cover 132, as discussed in detail above with respect to FIG. 6A.

Furthermore, regions of flexibility 190 are also provided between the outer cover 132 and the bodyside liner 130 where there is an absence of adhesive between adhesives 162a and 162b and an absence of adhesive between adhesives 162b and 162c. This area under the secondary first fastening components 126 in which the outer cover 132 is not coupled to the bodyside liner 130 provides for relative movement of the secondary first fastening components 126 with respect to the bodyside liner 130, as discussed above in detail with respect to FIG. 6B.

FIG. 6C also illustrates that regions of flexibility 190 can be provided between the bodyside liner 130 and the containment flaps 148. An absence of adhesive between adhesives 164a and 164b and an absence of adhesive between adhesives 164c and 164d provides for an area of the bodyside liner 130 under the secondary first fastening components 126 that is not coupled to the containment flaps 148. These regions of flexibility 190 between the bodyside liner 130 and the base 147 of each respective containment flap 148 allow for relative movement between the bodyside liner 130 and the containment flaps 148. Because the secondary first fastening components 126 are coupled to the bodyside liner 130 via the strip 180 and the outer cover 132, the secondary first fastening components 126 can move relative to the containment flaps 148 as well. The relative movement between the secondary first fastening components 126 and the containment flaps 48 can provide flexibility of the secondary fastening system when the wearer makes a movement (e.g., walks, crawls, runs, bends, etc.) that affects or binds the front portion 116 of the diaper 110, while still maintaining the positioning of the containment flaps 148 to retain proper gasketing properties.

For the multiple regions of flexibility 190 provided for in the embodiment illustrated in FIG. 6C, the diaper 110 can provide benefits of reducing the potential for red-marking and discomfort to a wearer in the area of the secondary first fastening components 126 as well as reduce the potential of pop-opens at the secondary first fastening components 126 (i.e., the secondary first fastening component 126 becoming disengaged from the secondary second fastening component 178). Although the regions of flexibility 190 in FIG. 6C each extend beyond both longitudinal sides 126a of each of the secondary first fastening components 126 and for the longitudinal length of the secondary first fastening component 126, it is contemplated that one or more of the regions of flexibility 190 do not extend past one or more of the longitudinal sides 126a of the secondary first fastening components 126 or for the entire length of the secondary first fastening component 126 in the longitudinal direction 112.

It is to be noted that although the diaper 110 in FIGS. 6A-6C illustrate that each of the secondary first fastening components 126 includes such a region of flexibility 190, it is contemplated that only one of the secondary first fastening components 126 (such as either the left or the right secondary first fastening component 126) can include such a region of flexibility 190 in the diaper 110. Furthermore, it can be appreciated that where more than one region of flexibility 190 exists under the secondary first fastening components 126, whether between two of the same components (such as the strip 180 and the outer cover 132) or between multiple different components (such as between the strip 180 and the outer cover 132 and between the bodyside liner 130 and a containment flap 148), such regions of flexibility 190 can be of different shapes and sizes and need not be symmetrical between the left and the right secondary first fastening components 126.

Figure 8:
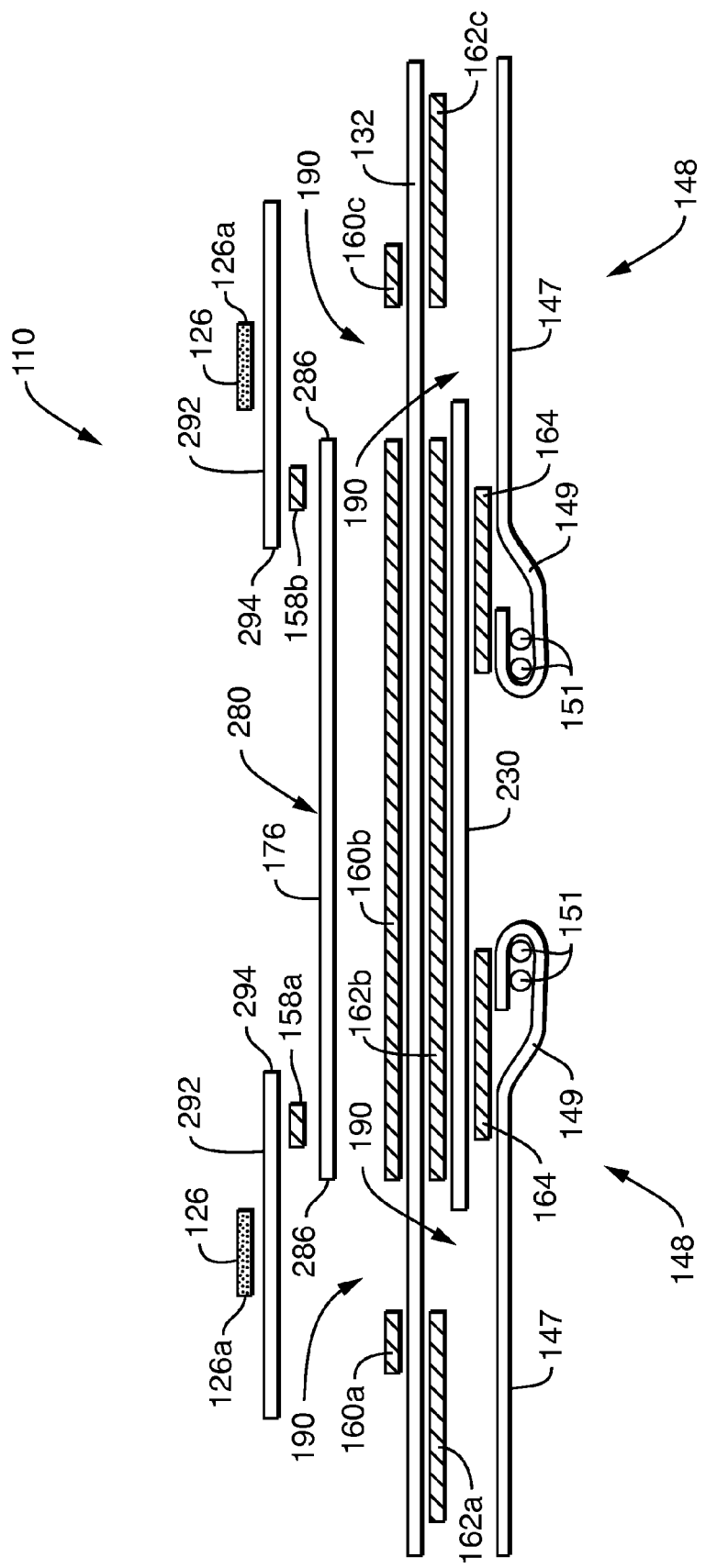
FIG. 8 is a cross-sectional view of the diaper of FIG. 7 taken along line 8-8 showing another configuration of coupling components of the diaper under the secondary first fastening components.

FIGS. 7 and 8 illustrate yet another suitable embodiment of the diaper 110 according to some aspects of the disclosure. FIG. 7 depicts the diaper 110 in an unfolded and laid flat condition to show the outer surface of the diaper 110 which faces away from the wearer when the diaper is worn. The majority of the operable aspects of the diaper 110 in FIG. 7 are the same or substantially similar to the embodiment of the diaper 110 depicted in the FIG. 5. In the embodiment depicted in FIGS. 7 and 8, the bodyside liner 230 does not extend to the longitudinal side edges 128 of the diaper 110. The bodyside liner 230 in conjunction with the containment flaps 148 form a three-part liner, as the containment flaps 148 extend to the longitudinal side edges 128 of the diaper 110 and are coupled to the bodyside liner 230 with adhesive 164.

In this embodiment, each of the secondary first fastening components 126 are provided on a corresponding carrier material 292 which is then attached to or otherwise provided on the outer cover 132. The outer edges 286 of a strip 280 (which includes primary second fastening component 176) overlap and attach to the carrier materials 292. That is, the innermost longitudinal edge 294 of each carrier material 292 is disposed inboard of a corresponding outer side edge 286 of the strip 280. In such embodiments, the carrier materials 292 may be embedded or otherwise provided to the outer cover 132 of the diaper 110 by overlapping and attaching to the strip 280 at a location near the outer side edges 286 of the strip 280, such as with adhesives 158a and 158b, as shown in FIG. 8. Alternatively, the carrier materials 292 may be coupled directly to the outer cover 132, transversely outside of the side edges 286 of the strip 280. In one suitable embodiment, the carrier materials 292 can be composed of a spunbond-meltblown-spunbond ("SMS") material, however, it can be appreciated by one of ordinary skill in the art that the carrier materials 292 can be composed of other suitable materials.

As illustrated in FIG. 8, the carrier materials 292 can be coupled to the outer cover 132 with adhesives 160a and 160c, as well as adhesive 160b. Additionally, the strip 280 can be coupled to the outer cover 132 with the adhesive 160b. The absence of adhesive between adhesives 160a and 160b as well as the absence of adhesive between adhesives 160b and 160c provides for regions of flexibility 190 between each carrier material 292 and the outer cover 132 under the secondary first fastening components 126. These regions of flexibility 190 provide for at least a portion of the area of the carrier materials 292 under the secondary first fastening components 126 not being coupled to the outer cover 132. Such regions of flexibility 190 provide for relative movement between the carrier materials 292 and the outer cover 132, and in turn, between the secondary first fastening components 126 and the outer cover 132 to provide the benefits of reducing the potential for discomfort and red-marking and reducing pop-opens as previously discussed.

FIG. 8 also illustrates that the outer cover 132 can be coupled to the bodyside liner 230 with adhesive 162b and can be coupled to the containment flaps 148 with adhesives 162a and 162c. Additionally, the bodyside liner 230 can be attached to the containment flaps 148 with adhesive 164. In the embodiment shown in FIG. 8, the adhesive 164 can couple at least a portion of the base 147 and at least a portion of the stem 149 of each containment flap 148 to the bodyside liner 230. In other embodiments, the stem 149 need not be coupled to the bodyside liner 230. The absence of adhesive between adhesives 162a and 162b and the absence of adhesive between adhesives 162b and 162c provides for regions of flexibility 190 between the outer cover 132 and the containment flaps 148, and specifically, between the outer cover 132 and the base 147 of each containment flap 148 in the embodiment depicted in FIG. 8. Depending on the positioning of secondary first fastening components 126 in the lateral direction 114, a region of flexibility 190 can exist between the outer cover 132 and the stem 149 of each containment flap 148, or between the bodyside liner 230 and the stem 149 of each containment flap 148, in alternative configurations. These regions of flexibility 190 provide for at least a portion of the area of the outer cover 132 under the secondary first fastening components 126 not being coupled to the containment flaps 148. These regions of flexibility 190 provide for relative movement between the outer cover 132 and the containment flaps 148, and specifically, between the outer cover 132 and the base 147 of each of the containment flaps 148 in the embodiment illustrated in FIG. 8. Because the secondary first fastening components 126 are coupled to the outer cover 132 via the carrier materials 292 and the strip 280, it follows then that the secondary first fastening components 126 can also move relative to a portion of the containment flaps 148 based on these regions of flexibility 190.

Although the regions of flexibility 190 in FIGS. 7 and 8 each extend beyond both longitudinal sides 126a of each of the secondary first fastening components 126 and for the entire length of the secondary first fastening component 126 in the longitudinal direction 112, it is contemplated that one or more of the regions of flexibility 190 do not extend past one or more of the longitudinal sides 126a of the secondary first fastening components 126 or for the entire longitudinal length of the secondary first fastening component 126. Additionally, it is to be noted that although the diaper 110 in FIGS. 7 and 8 illustrate that each of the secondary first fastening components 126 includes a region of flexibility 190, it is contemplated that only one of the secondary first fastening components 126 (such as either the left or the right secondary first fastening component 126) can include such a region of flexibility 190 in the diaper 110. Furthermore, it can be appreciated that where more than one region of flexibility 190 exists under the secondary first fastening components 126, whether between two of the same components (such as between the carrier materials 292 and the outer cover 132) or between multiple different components (such as between the carrier materials 292 and the outer cover 132 and between the outer cover 132 and a containment flap 148), such regions of flexibility 190 can be of different shapes and sizes and need not be symmetrical between the left and the right secondary first fastening components 126.

As will be appreciated by those skilled in the art, changes and variations to the present disclosure are considered to be within the ability of those skilled in the art. For example, where adhesives are used to join or couple various components of the diaper 110, it can be appreciated by one of ordinary skill in the art that other means and methods can be used to join or couple the same components of the diaper 110 while still being within the scope of the disclosure. Such alternative methods can include, but are not limited to, pressure bonding, ultrasonic bonding, thermal bonding, and stitching. As further appreciated by those skilled in the art, regions of flexibility 190 under secondary first fastening components 126 can occur between various layers or components of a diaper 110, other than the adjacent layers or components of the diaper 110 described above, yet still provide similar benefits as described herein. Other examples of changes are contained in the patents identified above, each of which is incorporated herein by reference in its entirety to the extent it is consistent with this specification. Such changes and variations are intended by the inventors to be within the scope of the present disclosure. It is also to be understood that the scope of the present disclosure is not to be interpreted as limited to the specific aspects disclosed herein, but only in accordance with the appended claims when read in light of the foregoing disclosure.

What is claimed is:

1. An absorbent article comprising:
    an absorbent assembly comprising a liquid impermeable outer cover, a liquid permeable bodyside liner, and an absorbent body disposed between the outer cover and the bodyside liner, the absorbent assembly including a front waist region, a rear waist region, and a crotch region extending between the front waist region and the rear waist region;
    a pair of ears extending transversely outward from opposite sides of the absorbent assembly;
    a fastening system configured to attach the rear waist region to the front waist region to define a wear configuration of the absorbent article, the fastening system comprising a primary fastening system and a secondary fastening system;
    wherein the secondary fastening system includes at least one secondary first fastening component and at least one secondary second fastening component, the at least one secondary first fastening component being coupled to a first carrier material,
    wherein the first carrier material has an outward facing surface and an inward facing surface, the secondary first fastening component being coupled to the outward facing surface of the first carrier material,
    wherein the inward facing surface of the first carrier material is coupled to the outer cover in the front waist region, and at least a portion of an area of the inward facing surface of the first carrier material under the at least one secondary first fastening component is not coupled to the outer cover.

2. The absorbent article of claim 1, wherein substantially all of the area of the inward facing surface of the first carrier material under the at least one secondary first fastening component is not coupled to the outer cover.

3. The absorbent article of claim 1, wherein the secondary fastening system includes a left secondary first fastening component and a right secondary first fastening component.

4. The absorbent article of claim 3, wherein both the left secondary first fastening component and the right secondary first fastening component are coupled to the outward facing surface of the first carrier material, and wherein both the left secondary first fastening component and the right secondary first fastening component are configured such that at least a portion of an area of the inward facing surface of the first carrier material under the left and right secondary first fastening components is not coupled to the outer cover.

5. The absorbent article of claim 3, wherein the left secondary first fastening component is coupled to the outward facing surface of the first carrier material and the right secondary first fastening component is coupled to an outward facing surface of a second carrier material, the second carrier material being separate from the first carrier material, wherein at least a portion of an inward facing surface of the second carrier material under the right secondary first fastening component is not coupled to the outer cover.

6. The absorbent article of claim 1, wherein the at least one secondary first fastening component comprises a hook material and the at least one secondary second fastening component comprises a loop material.

7. The absorbent article of claim 1, wherein the primary fastening system includes at least one primary first fastening component and a primary second fastening component, wherein the first carrier material forms the primary second fastening component.

8. An absorbent article comprising:
    an absorbent assembly comprising a liquid impermeable outer cover, a liquid permeable bodyside liner, and an absorbent body disposed between the outer cover and the bodyside liner, the absorbent assembly including a front waist region, a rear waist region, and a crotch region extending between the front waist region and the rear waist region;
    a pair of ears extending transversely outward from opposite sides of the absorbent assembly;
    a fastening system configured to attach the rear waist region to the front waist region to define a wear configuration of the absorbent article, the fastening system comprising a primary fastening system and a secondary fastening system;
    wherein the secondary fastening system includes at least one secondary first fastening component and at least one secondary second fastening component, the at least one secondary first fastening component being coupled to the outer cover, the bodyside liner extending under the at least one secondary first fastening component, and at least a portion of an area of the outer cover under the at least one secondary first fastening component is not coupled to the bodyside liner.

9. The absorbent article of claim 8, wherein substantially all of the area of the outer cover under the at least one secondary first fastening component is not coupled to the bodyside liner.

10. The absorbent article of claim 8, wherein the at least one secondary first fastening component is coupled to a carrier material, the carrier material being coupled to the outer cover.

11. The absorbent article of claim 10, wherein the carrier material forms part of the primary fastening system.

12. The absorbent article of claim 10, wherein at least a portion of an area of the carrier material under the at least one secondary first fastening component is not coupled to the outer cover.

13. The absorbent article of claim 12, wherein substantially all of the area of the carrier material under the at least one secondary first fastening component is not coupled to the outer cover.

14. The absorbent article of claim 8, wherein the secondary fastening system includes a left secondary first fastening component and a right secondary first fastening component.

15. The absorbent article of claim 14, wherein the bodyside liner extends under the left secondary first fastening component and the right secondary first fastening component, and both the left secondary first fastening component and the right secondary first fastening component are configured such that at least a portion of an area of the outer cover under the left and right secondary first fastening components is not coupled to the bodyside liner.

16. An absorbent article comprising:
an absorbent assembly comprising a liquid impermeable outer cover, a liquid permeable bodyside liner, and an absorbent body disposed between the outer cover and the bodyside liner, the absorbent assembly including a front waist region including a front waist edge, a rear waist region including a rear waist edge, a crotch region extending between the front waist region and the rear waist region, and two side edges extending between the front waist edge and the rear waist edge;
a pair of ears extending transversely outward from the absorbent assembly, the pair of ears including a left ear and a right ear;
a pair of containment flaps on opposite sides of the absorbent body including a first containment flap and a second containment flap, the first and the second containment flaps including a stem and a base, the base being coupled to the outer cover;
a fastening system configured to attach the rear waist region to the front waist region to define a wear configuration of the absorbent article, the fastening system comprising a primary fastening system and a secondary fastening system;
wherein the secondary fastening system includes at least one secondary first fastening component and at least one secondary second fastening component, the at least one secondary first fastening component is coupled to an outward facing surface of a first carrier material, the first carrier material further comprising an inward facing surface, the inward facing surface being coupled to the outer cover, the first containment flap extending under the at least one secondary first fastening component, at least a portion of an area of the outer cover under the at least one secondary first fastening component is not coupled to the first containment flap, and at least a portion of an area of the inward facing surface of the first carrier material under the at least one secondary first fastening component is not coupled to the outer cover.

17. The absorbent article of claim 16, wherein substantially all of the area of the outer cover under the at least one secondary first fastening component is not coupled to the first containment flap.

18. The absorbent article of claim 16, wherein the base of the first containment flap extends under the at least one secondary first fastening component and at least a portion of an area of the outer cover under that at least one secondary first fastening component is not coupled to the base of the first containment flap.

19. The absorbent article of claim 16, wherein the first carrier material forms part of the primary fastening system.

20. The absorbent article of claim 16, wherein substantially all of the area of the inward facing surface of the first carrier material under the at least one secondary first fastening component is not coupled to the outer cover.

21. The absorbent article of claim 16, wherein the secondary fastening system includes a left secondary first fastening component and a right secondary first fastening component.

22. The absorbent article of claim 21, wherein the left secondary first fastening component is coupled to the outward facing surface of the first carrier material and the right secondary first fastening component is coupled to an outward facing surface of a second carrier material, the second carrier material being separate from the first carrier material.

23. The absorbent article of claim 22, wherein the first containment flap extends under the left secondary first fastening component, the second containment flap extends under the right secondary first fastening component, and at least a portion of an area of the outer cover under the right secondary first fastening component is not coupled to the second containment flap.

24. The absorbent article of claim 23, wherein the left secondary first fastening component is coupled to the outward facing surface of the first carrier material and the right secondary first fastening component is coupled to the outward facing surface of the second carrier material, the second carrier material being separate from the first carrier material, and wherein at least a portion of the inward facing surface of the first carrier material under the left secondary first fastening component is not coupled to the outer cover and at least a portion of an inward facing surface of the second carrier material under the right secondary first fastening component is not coupled to the outer cover.

25. An absorbent article comprising:
an absorbent assembly comprising a liquid impermeable outer cover, a liquid permeable bodyside liner, and an absorbent body disposed between the outer cover and the bodyside liner, the absorbent assembly including a front waist region, a rear waist region, and a crotch region extending between the front waist region and the rear waist region;
a pair of ears extending transversely outward from opposite sides of the absorbent assembly; and
a fastening system configured to attach the rear waist region to the front waist region to define a wear configuration of the absorbent article, the fastening system comprising a primary fastening system and a secondary fastening system, the secondary fastening system includes at least one secondary first fastening component and at least one secondary second fastening component, the at least one secondary first fastening component being coupled to a first carrier material, the first carrier material being coupled to the outer cover in the front waist region;

wherein at least one region of flexibility is provided between adjacent components of the absorbent article between the at least one secondary first fastening component and the bodyside liner in an area under the at least one secondary first fastening component.

26. The absorbent article of claim 25, wherein the at least one region of flexibility is between the first carrier material and the outer cover.

27. The absorbent article of claim 25, wherein the at least one region of flexibility is between the outer cover and the bodyside liner.

28. The absorbent article of claim 25, wherein the secondary fastening system includes a left secondary first fastening component and a right secondary first fastening component, and wherein at least one region of flexibility is provided between adjacent components of the absorbent article between the left secondary first fastening component and the bodyside liner in an area under the left secondary first fastening component and at least one region of flexibility is provided between adjacent components of the absorbent article between the right secondary first fastening component and the bodyside liner in an area under the right secondary first fastening component.

* * * * *